US011577088B2

(12) United States Patent
Zhang et al.

(10) Patent No.: US 11,577,088 B2
(45) **Date of Patent: *Feb. 14, 2023**

(54) USE OF CHARGE IMBALANCED PULSES IN AN IMPLANTABLE STIMULATOR TO EFFECT A PSEUDO-CONSTANT DC CURRENT BIAS

(71) Applicant: Boston Scientific Neuromodulation Corporation, Valencia, CA (US)

(72) Inventors: Tianhe Zhang, Studio City, CA (US); G. Karl Steinke, Valencia, CA (US); Matthew L. McDonald, Pasadena, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 200 days.

This patent is subject to a terminal disclaimer.

(21) Appl. No.: 17/152,412

(22) Filed: Jan. 19, 2021

(65) Prior Publication Data

US 2021/0162222 A1 Jun. 3, 2021

Related U.S. Application Data

(63) Continuation of application No. 16/210,814, filed on Dec. 5, 2018, now Pat. No. 10,926,097.

(Continued)

(51) Int. Cl.
*A61N 1/378* (2006.01)
*A61N 1/36* (2006.01)
(Continued)

(52) U.S. Cl.
CPC ....... *A61N 1/3787* (2013.01); *A61N 1/36125* (2013.01); *A61N 1/3754* (2013.01);
(Continued)

(58) Field of Classification Search
CPC .............. A61N 1/3787; A61N 1/36125; A61N 1/37248; A61N 1/37252; A61N 1/3754; A61N 1/36071; A61N 1/3756
See application file for complete search history.

(56) References Cited

U.S. PATENT DOCUMENTS 5,713,926 A 2/1998 Hauser et al.
6,181,969 B1 1/2001 Gord
(Continued)

FOREIGN PATENT DOCUMENTS

WO 2014/035731 3/2014

OTHER PUBLICATIONS

M. Bikson et al. "Effects of Uniform Extracellular DC Electric Fields on Excitability in Rat Hippocampal Slices In Vitro," J. Physiology 557.1, pp. 175-190 (2004).

(Continued)

*Primary Examiner* — Brian T Gedeon
(74) *Attorney, Agent, or Firm* — Lewis & Reese, PLLC

(57) ABSTRACT

Techniques are described for providing a therapeutic pseudo-constant DC current in an implantable stimulator using pulses whose positive and negative phases are not charge balanced. Such charge imbalanced pulses act to charge any capacitance in the current path between selected electrode nodes, such as the DC-blocking capacitors and/or any inherent capacitance such as those present at the electrode/tissue interface. These charged capacitances act during quiet periods between the pulses to induce a pseudo-constant DC current. Beneficially, these DC currents can be small enough to stay within charge density limits and hence not corrode the electrode or cause tissue damage, and further can be controlled to stay within such limits or for other reasons. Graphical user interface (GUI) aspects for generating the (Continued)

charge imbalanced pulses and for determining and/or controlling the pseudo-constant DC current are also provided.

20 Claims, 10 Drawing Sheets

Related U.S. Application Data

(60) Provisional application No. 62/599,546, filed on Dec. 15, 2017.

(51) Int. Cl.
*A61N 1/372* (2006.01)
*A61N 1/375* (2006.01)

(52) U.S. Cl.
CPC ..... *A61N 1/37247* (2013.01); *A61N 1/37252* (2013.01); *A61N 1/36071* (2013.01); *A61N 1/3756* (2013.01)

(56) References Cited

U.S. PATENT DOCUMENTS

| | | | |
|---|---|---|---|
| 6,516,227 | B1 | 2/2003 | Meadows et al. |
| 6,560,490 | B2 | 5/2003 | Grill et al. |
| 6,690,974 | B2 | 2/2004 | Archer et al. |
| 7,813,804 | B1 | 10/2010 | Jaax |
| 8,983,614 | B2 | 3/2015 | Kilgore et al. |
| 9,061,140 | B2 | 6/2015 | Shi et al. |
| 9,259,574 | B2 | 2/2016 | Aghassian |
| 9,694,178 | B2 | 7/2017 | Ruffini et al. |
| 2007/0038250 | A1 | 2/2007 | He et al. |
| 2007/0100399 | A1 | 5/2007 | Parramon et al. |
| 2012/0092031 | A1 | 4/2012 | Shi et al. |
| 2012/0095519 | A1 | 4/2012 | Parramon et al. |
| 2012/0095529 | A1 | 4/2012 | Parramon et al. |
| 2013/0289661 | A1 | 10/2013 | Griffith et al. |
| 2013/0289665 | A1 | 10/2013 | Mamfeldt et al. |
| 2015/0080982 | A1 | 3/2015 | Funderburk |
| 2015/0157861 | A1 | 6/2015 | Aghassian |
| 2015/0231402 | A1 | 8/2015 | Aghassian |
| 2015/0360038 | A1 | 12/2015 | Zottola et al. |
| 2016/0121126 | A1 | 5/2016 | Marnfeldt |
| 2016/0220820 | A1 | 8/2016 | Zottola |
| 2017/0259069 | A1 | 9/2017 | Bam et al. |
| 2017/0319109 | A1 | 11/2017 | Skelton et al. |
| 2018/0071527 | A1 | 3/2018 | Feldman et al. |
| 2018/0110992 | A1 | 4/2018 | Parramon et al. |
| 2018/0140831 | A1 | 5/2018 | Feldman et al. |
| 2018/0369593 | A1 | 12/2018 | Johanek |

OTHER PUBLICATIONS

D.R. Merrill et al., "Electrical Stimulation of Excitable Tissue: Design of Efficacious and Safe Protocols," J. Neuroscience Methods, 141: 171-98 (2005).
R.V. Shannon, "A Model of Safe Levels for Electrical Stimulation.," IEEE Trans. on Biomedical Eng'g, vol. 39, pp. 424-426 (1992).
D. Kumsa et al., "Electrical Neurostimluation with Imbalanced Waveform Mitigates Dissolution of Platinum Electrodes," J. Neural Eng'g, 13, 054001 (2016).
A. Rahman et al., "Cellular Effects of Acute Direct Current Stimulation: Somatic and Synaptic Terminal Effects," J. Physiology, 591.10, pp. 2563-2578 (2013).
K. L. Kilgore et al., "Nerve Conduction Block Utilising High-Frequency Alternating Current," Medical & Biological Eng'g & Computing, vol. 42, pp. 394-406 (2004).

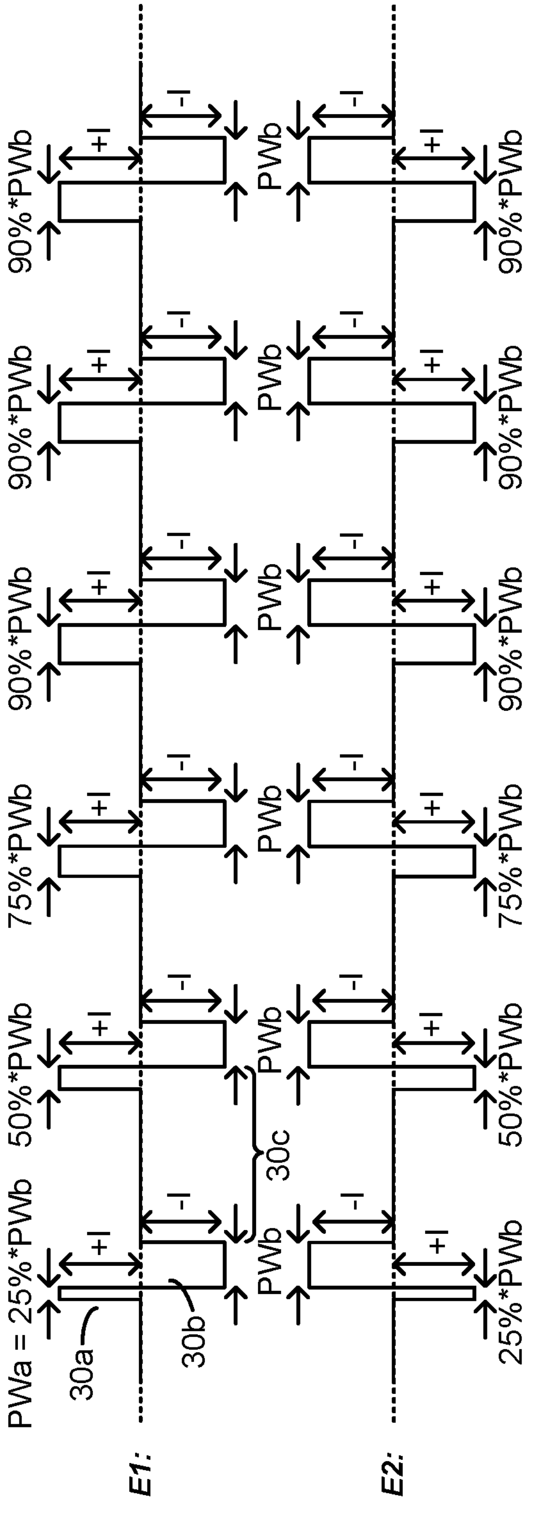
Figure 7
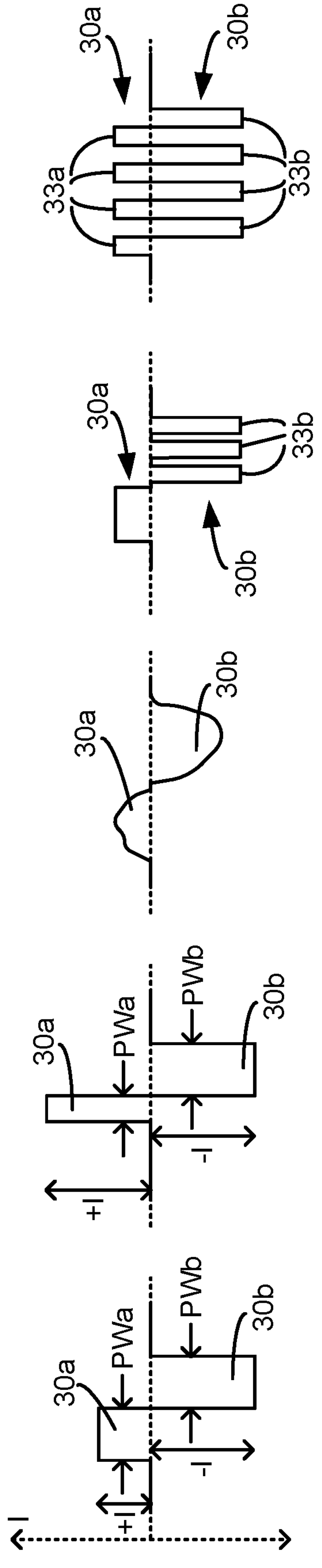
Figure 8A
Figure 8B
Figure 8C
Figure 8D
Figure 8E

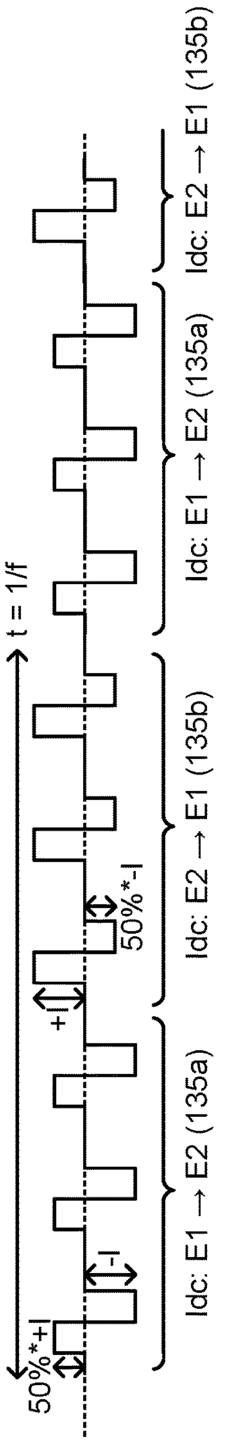
Figure 15D
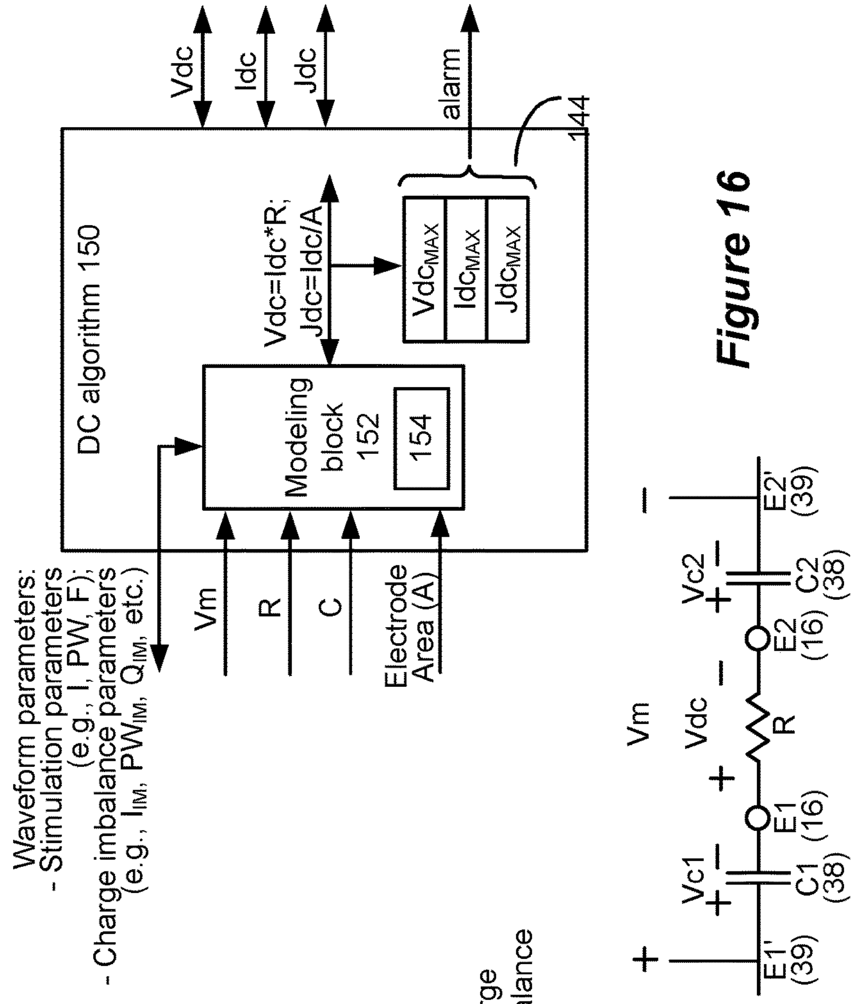
Figure 16
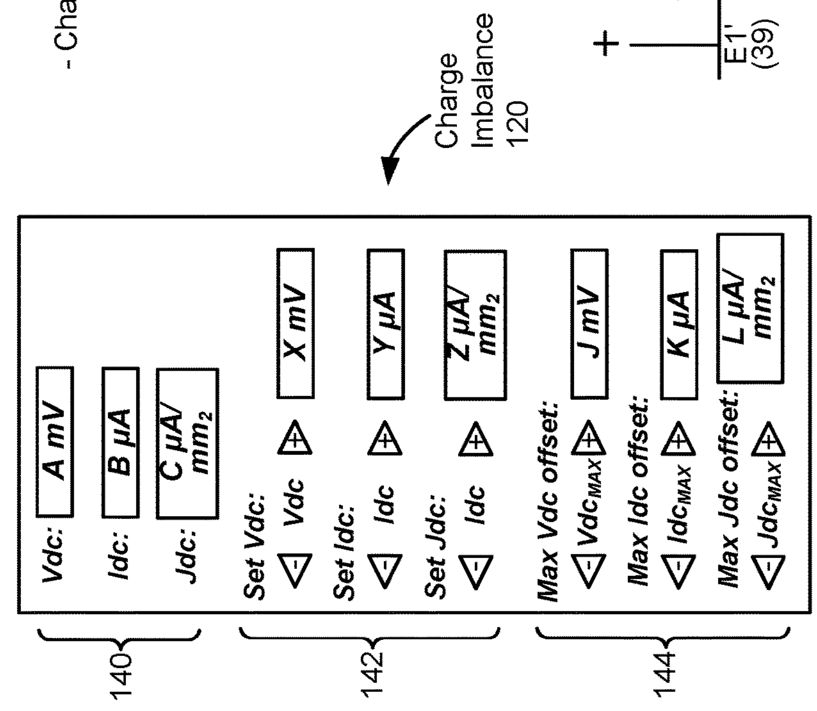

USE OF CHARGE IMBALANCED PULSES IN AN IMPLANTABLE STIMULATOR TO EFFECT A PSEUDO-CONSTANT DC CURRENT BIAS

CROSS REFERENCE TO RELATED APPLICATIONS

This is a continuation of U.S. patent application Ser. No. 16/210,814, filed Dec. 5, 2018 (allowed), which is a non-provisional of U.S. Provisional Patent Application Ser. No. 62/599,546, filed Dec. 15, 2017. These applications are incorporated herein by reference in its entirety, and priority is claimed to both.

FIELD OF THE INVENTION

This application relates to Implantable Medical Devices (IMDs), and more specifically to techniques for creating a DC current in implantable neurostimulation systems.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable neurostimulator device system.

An SCS system typically includes an Implantable Pulse Generator (IPG) 10 shown in FIG. 1. The IPG 10 includes a biocompatible device case 12 that holds the IPG's circuitry and a battery 14 for providing power for the IPG to function. The IPG 10 is coupled to tissue-stimulating electrodes 16 via one or more electrode leads that form an electrode array 17. For example, one or more percutaneous leads 15 can be used having ring-shaped or split-ring electrodes 16 carried on a flexible body 18. In another example, a paddle lead 19 provides electrodes 16 positioned on one of its generally flat surfaces. Lead wires 20 within the leads are coupled to proximal contacts 21, which are insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12, which stimulation circuitry 28 is described below.

In the illustrated IPG 10, there are thirty-two electrodes (E1-E32), split between four percutaneous leads 15, or contained on a single paddle lead 19, and thus the header 23 may include a 2×2 array of eight-electrode lead connectors 22. However, the type and number of leads, and the number of electrodes, in an IPG is application specific and therefore can vary. The conductive case 12 can also comprise an electrode (Ec). In a SCS application, the electrode lead(s) are typically implanted in the spinal column proximate to the dura in a patient's spinal cord, preferably spanning left and right of the patient's spinal column. The proximal contacts 21 are then tunneled through the patient's tissue to a distant location such as the buttocks where the IPG case 12 is implanted, where they are coupled to the lead connectors 22. In other IPG examples designed for implantation directly at a site requiring stimulation, the IPG can be lead-less, having electrodes 16 instead appearing on the body of the IPG 10 for contacting the patient's tissue. The IPG lead(s) can be integrated with and permanently connected to the IPG 10 in other solutions. The goal of SCS therapy is to provide electrical stimulation from the electrodes 16 to alleviate a patient's symptoms, such as chronic back pain.

IPG 10 can include an antenna 27*a* allowing it to communicate bi-directionally with a number of external devices discussed subsequently. Antenna 27*a* as shown comprises a conductive coil within the case 12, although the coil antenna 27*a* can also appear in the header 23. When antenna 27*a* is configured as a coil, communication with external devices preferably occurs using near-field magnetic induction. IPG 10 may also include a Radio-Frequency (RF) antenna 27*b*. RF antenna 27*b* is shown within the header 23, but it may also be within the case 12. RF antenna 27*b* may comprise a patch, slot, or wire, and may operate as a monopole or dipole. RF antenna 27*b* preferably communicates using far-field electromagnetic waves, and may operate in accordance with any number of known RF communication standards, such as Bluetooth, Zigbee, WiFi, MICS, and the like.

Stimulation in IPG 10 is typically provided by a sequence of pulses (or waveforms more generally) each of which may include a number of phases such as 30*a* and 30*b*, as shown in the example of FIG. 2A. Stimulation parameters typically include amplitude (current I, although a voltage amplitude V can also be used); frequency (F); pulse width (PW) of the pulses or of its individual phases such as 30*a* and 30*b*; the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 28 in the IPG 10 can execute to provide therapeutic stimulation to a patient.

In the example of FIG. 2A, electrode E1 has been selected as an anode (during first pulse phases 30*a*), and thus provides pulses which source a positive current of amplitude +I to the tissue. Electrode E2 has been selected as a cathode (again during first phases 30*a*), and thus provides pulses which sink a corresponding negative current of amplitude −I from the tissue. This is an example of bipolar stimulation, in which only lead-based electrodes are used to provide stimulation to the tissue (one anode, one cathode). However, more than one electrode may be selected to act as an anode at a given time, and more than one electrode may be selected to act as a cathode at a given time.

IPG 10 as mentioned includes stimulation circuitry 28 to form prescribed stimulation at a patient's tissue. FIG. 3 shows an example of stimulation circuitry 28, which includes one or more current sources 40 and one or more current sinks 42. The sources and sinks 40 and 42 can comprise Digital-to-Analog converters (DACs), and may be referred to as PDACs 40 and NDACs 42 in accordance with the Positive (anodic) and Negative (cathodic) currents they respectively issue. The sourced and sunk current from one or more selected PDACs 40 or NDACs 42 are respectively directed in this example by switch matrices 44 and 46 to selected electrode nodes Ei' 39 coupled to the electrodes Ei 16. Although not shown, the DACs 40 and 42 and switch matrices 44 and 46 receive digital information regarding the stimulation parameters to form the stimulation at selected electrodes with the correct amplitude and timing. The stimulation circuitry 28 in this example also supports selection of the conductive case 12 as an electrode (Ec 12), which case electrode is typically selected for monopolar stimulation. DACs 40 and 42 can also comprise voltage sources.

Proper control of the DACs 40 and 42 and the switching matrices 44 and 46 allows any of the electrodes 16 to act as anodes or cathodes to create a current through a patient's tissue, R, hopefully with beneficial therapeutic effect. In the example shown, PDAC $40_2$ is selected to source a current of amplitude I to electrode node E1' and to anode electrode E1 via switch matrix 44, while NDAC $42_1$ is selected to sink a current of amplitude I from electrode node E2' and cathode electrode E2 via switching matrix 46. Other PDACs 40 and NDACs 42, or one of more of each, could also have been selected to produce +I at E1 and –I at E2. Power for the stimulation circuitry 28 is provided by a compliance voltage VH, as described in further detail in U.S. Patent Application Publication 2013/0289665. More than one anode electrode and more than one cathode electrode may be selected at one time, and thus current can flow through the tissue R between two or more of the electrodes 16.

Other stimulation circuitries 28 can also be used in the IPG 10. For example, in an example not using switching matrices, each electrode node Ei' 39 can be hardwired to a dedicated PDAC 40*i* and a dedicated NDAC 42*i*, such as is disclosed in U.S. Pat. No. 6,181,969 for example. In another example, the PDACs 40 and NDACs 42 may provide currents of fixed amplitudes, with multiple of these DACs being selected by the switching matrices 44 and 46 to provide a sum of their currents at a selected electrode node, such as described in U.S. Patent Application Publications 2007/0038250 and 2007/0100399.

Much of the stimulation circuitry 28 of FIG. 3, including the DACs 40 and 42, the switch matrices 44 and 46, and the electrode nodes Ei' 39 can be integrated on one or more Application Specific Integrated Circuits (ASICs), as described in U.S. Patent Application Publications 2012/0095529, 2012/0092031, and 2012/0095519. As explained in these references, ASIC(s) may also contain other circuitry useful in the IPG 10, such as telemetry circuitry (for interfacing off chip with telemetry antennas 27*a* and/or 27*b*), circuitry for generating the compliance voltage VH, various measurement circuits, etc.

Also shown in FIG. 3 are DC-blocking capacitors Ci 38, which are placed in series in the current paths between each of the electrode nodes Ei' 39 and the electrodes Ei 16/case electrode Ec 12. The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. Patent Application Publication 2015/0157861.

Referring again to FIG. 2A, the stimulation pulses as shown are biphasic, with each pulse comprising a first phase 30*a* followed thereafter by a second phase 30*b* of opposite polarity. (Although not shown, an interphase period during which no active current is driven may intervene between the phases 30*a* and 30*b*). Biphasic pulses are useful to actively recover any charge that might be stored on capacitive elements in the current path, such as on the DC-blocking capacitors 38. Charge recovery is shown with reference to both FIGS. 2A and 2B. During the first pulse phases 30*a*, charge will build up across the DC-blocking capacitors C1 and C2 associated with the electrodes E1 and E2 selected to produce the current, giving rise to voltages Vc1 and Vc2. Given the definition of these voltages in FIG. 2B, they are of the same polarity as shown in FIG. 2A. During the second pulse phases 30*b*, when the polarity of the current I is reversed at the selected electrodes E1 and E2, the stored charge on capacitors C1 and C2 is recovered, and thus voltages Vc1 and Vc2 return to 0V at the end the second pulse phase 30*b*.

To recover all charge by the end of the second pulse phase 30*b* of each pulse (Vc1=Vc2=0V), the first and second phases 30*a* and 30*b* are charged balanced. In the example shown, such charge balancing is achieved by using the same pulse width (PWa=PWb) and the same amplitude (|+I|=|–I|) for each of the pulse phases 30*a* and 30*b*. However, the pulse phases 30*a* and 30*b* may also be charged balance if the product of the amplitude and pulse width of each phase is equal, as is known.

FIG. 4 shows an external trial stimulation environment that may precede implantation of an IPG 10 in a patient. During external trial stimulation, stimulation can be tried on a prospective implant patient without going so far as to implant the IPG 10. Instead, one or more trial electrode arrays 17' (e.g., one or more trial percutaneous leads 15 or trial paddle leads 19) are implanted in the patient's tissue at a target location 52, such as within the spinal column as explained earlier. The proximal ends of the trial electrode array(s) 17' exit an incision 54 and are connected to an External Trial Stimulator (ETS) 50. The ETS 50 generally mimics operation of the IPG 10, and thus can provide stimulation to the patient's tissue as explained above. See, e.g., U.S. Pat. No. 9,259,574, disclosing a design for an ETS. The ETS 50 is generally worn externally by the patient for a short while (e.g., two weeks), which allows the patient and his clinician to experiment with different stimulation parameters to hopefully find a stimulation program that alleviates the patient's symptoms (e.g., pain). If external trial stimulation proves successful, the trial electrode array(s) 17' are explanted, and a full IPG 10 and a permanent electrode array 17 (e.g., one or more percutaneous 15 or paddle 19 leads) are implanted as described above; if unsuccessful, the trial electrode array(s) 17' are simply explanted.

Like the IPG 10, the ETS 50 can include one or more antennas to enable bi-directional communications with external devices such as those shown in FIG. 5. Such antennas can include a near-field magnetic-induction coil antenna 56*a*, and/or a far-field RF antenna 56*b*, as described earlier. ETS 50 may also include stimulation circuitry 58 (FIG. 4) able to form stimulation in accordance with a stimulation program, which circuitry may be similar to or comprise the same stimulation circuitry 28 present in the IPG 10. ETS 50 may also include a battery (not shown) for operational power.

FIG. 5 shows various external devices that can wirelessly communicate data with the IPG 10 and the ETS 50, including a patient hand-held external controller 60, and a clinician programmer 70. Both of devices 60 and 70 can be used to wirelessly transmit a stimulation program to the IPG 10 or ETS 50—that is, to program their stimulation circuitries 28 and 58 to produce stimulation with a desired amplitude and timing described earlier. Both devices 60 and 70 may also be used to adjust one or more stimulation parameters of a stimulation program that the IPG 10 or ETS 50 is currently executing. Devices 60 and 70 may also wirelessly receive information from the IPG 10 or ETS 50, such as various status information, etc.

External controller 60 can be as described in U.S. Patent Application Publication 2015/0080982 for example, and may comprise a controller dedicated to work with the IPG 10 or ETS 50. External controller 60 may also comprise a general purpose mobile electronics device such as a mobile phone which has been programmed with a Medical Device Application (MDA) allowing it to work as a wireless controller for the IPG 10 or ETS 50, as described in U.S. Patent Application Publication 2015/0231402. External controller 60 includes a Graphical User Interface (GUI), preferably including means for entering commands (e.g., buttons or selectable graphical icons) and a display 62. The external controller 60's GUI enables a patient to adjust stimulation parameters, although it may have limited functionality when compared to the more-powerful clinician programmer 70, described shortly.

The external controller 60 can have one or more antennas capable of communicating with the IPG 10 and ETS 50. For example, the external controller 60 can have a near-field magnetic-induction coil antenna 64*a* capable of wirelessly communicating with the coil antenna 27*a* or 56*a* in the IPG 10 or ETS 50. The external controller 60 can also have a far-field RF antenna 64*b* capable of wirelessly communicating with the RF antenna 27*b* or 56*b* in the IPG 10 or ETS 50.

Clinician programmer 70 is described further in U.S. Patent Application Publication 2015/0360038, and can comprise a computing device 72, such as a desktop, laptop, or notebook computer, a tablet, a mobile smart phone, a Personal Data Assistant (PDA)-type mobile computing device, etc. In FIG. 5, computing device 72 is shown as a laptop computer that includes typical computer user interface means such as a screen 74, a mouse, a keyboard, speakers, a stylus, a printer, etc., not all of which are shown for convenience. Also shown in FIG. 5 are accessory devices for the clinician programmer 70 that are usually specific to its operation as a stimulation controller, such as a communication "wand" 76 coupleable to suitable ports on the computing device 72, such as USB ports 79 for example.

The antenna used in the clinician programmer 70 to communicate with the IPG 10 or ETS 50 can depend on the type of antennas included in those devices. If the patient's IPG 10 or ETS 50 includes a coil antenna 27*a* or 56*a*, wand 76 can likewise include a coil antenna 80*a* to establish near-field magnetic-induction communications at small distances. In this instance, the wand 76 may be affixed in close proximity to the patient, such as by placing the wand 76 in a belt or holster wearable by the patient and proximate to the patient's IPG 10 or ETS 50. If the IPG 10 or ETS 50 includes an RF antenna 27*b* or 56*b*, the wand 76, the computing device 72, or both, can likewise include an RF antenna 80*b* to establish communication with the IPG 10 or ETS 50 at larger distances. The clinician programmer 70 can also communicate with other devices and networks, such as the Internet, either wirelessly or via a wired link provided at an Ethernet or network port.

To program stimulation programs or parameters for the IPG 10 or ETS 50, the clinician interfaces with a clinician programmer GUI 82 provided on the display 74 of the computing device 72. As one skilled in the art understands, the GUI 82 can be rendered by execution of clinician programmer software 84 stored in the computing device 72, which software may be stored in the device's non-volatile memory 86. Execution of the clinician programmer software 84 in the computing device 72 can be facilitated by control circuitry 88 such as one or more microprocessors, microcomputers, FPGAs, DSPs, other digital logic structures, etc., which are capable of executing programs in a computing device, and which may comprise their own memories. In one example, control circuitry 88 may comprise an i5 processor manufactured by Intel Corp., as described at https://www.intel.com/content/www/us/en/products/processors/core/i5-processors.html. Such control circuitry 88, in addition to executing the clinician programmer software 84 and rendering the GUI 82, can also enable communications via antennas 80*a* or 80*b* to communicate stimulation parameters chosen through the GUI 82 to the patient's IPG 10 or ETS 50.

The GUI of the external controller 60 may provide similar functionality because the external controller 60 can include the same hardware and software programming as the clinician programmer. For example, the external controller 60 includes control circuitry 66 similar to the control circuitry 88 in the clinician programmer 70, and may similarly be programmed with external controller software stored in device memory.

SUMMARY

In a first example, a system is disclosed, which may comprise: an external device configured to program an implantable stimulator device comprising a plurality of electrodes configured to contact a patient's tissue, wherein the external device comprises control circuitry configured to: generate a graphical user interface (GUI) at the external device; receive, via the GUI, selection of a plurality of parameters defining a sequence of waveforms to be provided to at least two of the electrodes, wherein each waveform comprises a positive phase and a negative phase, wherein one of the parameters comprises a charge imbalance parameter that sets a charge imbalance between the positive phase and the negative phase of at least one waveform in the sequence of waveforms; and transmit information to the implantable stimulator device, wherein the information is configured to program the implantable stimulator device to provide electrical stimulation at the at least two electrodes in accordance with the defined sequence of waveforms.

The plurality of parameters may comprise at least one of: an amplitude of at least one waveform in the sequence of waveforms, a pulse width of at least one waveform in the sequence of waveforms, a pulse width of the positive phase or the negative phase of at least one waveform in the sequence of sequence of waveforms, or a frequency at which waveforms are provided in the sequence of waveforms. The control circuitry may be further configured to receive, via the GUI, selection of the at least two electrodes. In the defined sequence of waveforms, a total anodic current sourced to at least one of the at least two electrodes may equal a total cathodic current sunk to at least one of the at least two electrodes.

The charge imbalance parameter may comprise a difference between the positive phase and the negative phase of the at least one waveform. The difference may comprise a difference in amplitude, a difference in pulse width, or a difference in charge. The difference may be expressed as a ratio, a percentage, or a differential. The charge imbalance parameter may set a charge imbalance between the positive phase and the negative phase of each waveform in the sequence of waveforms.

The control circuitry may be further configured to use the plurality of parameters to determine a pseudo-constant DC current, DC voltage or DC current density to be formed between the at least two electrodes during quiet periods between waveforms in the sequence of waveforms. The GUI may be configured to display the determined pseudo-constant DC current, DC voltage or DC current density. The control circuitry may also be further configured to receive, via the GUI, an input specifying a pseudo-constant DC current, DC voltage or DC current density to be formed between the at least two electrodes during quiet periods between waveforms in the sequence of waveforms. The control circuitry may be further configured to determine the charge imbalance parameter based on the specified pseudo-constant DC current, DC voltage or DC current density.

In a second example, a non-transitory computer readable media is disclosed which may comprise instructions executable on an external device for programming an implantable stimulator device, wherein the implantable stimulator device comprises a plurality of electrodes configured to contact a patient's tissue, wherein the instructions when executed are configured to enable control circuitry in the external device to: generate a graphical user interface (GUI) at the external device; and receive, via the GUI, selection of a plurality of parameters defining a sequence of waveforms to be provided to at least two of the electrodes, wherein each waveform comprises a positive phase and a negative phase, wherein one of the parameters comprises a charge imbalance parameter that sets a charge imbalance between the positive phase and the negative phase of at least one waveform in the sequence of waveforms.

The instructions when executed may be further configured to enable control circuitry in the external device to: transmit information to the implantable stimulator device, wherein the information is configured to program the implantable stimulator device to provide electrical stimulation at the at least two electrodes in accordance with the defined sequence of waveforms. The non-transitory computer readable media may further comprise instructions for any of the concepts mentioned in the first example.

In a third example, a method is disclosed for programming an implantable stimulator device comprising a plurality of electrodes configured to contact a patient's tissue, which method may comprise: using a graphical user interface (GUI) of an external device to define a sequence of waveforms to be provided at at least two of the electrodes, wherein each waveform comprises a positive phase and a negative phase; using the GUI to further set a charge imbalance between the positive phase and the negative phase of at least one waveform in the sequence of waveforms; and transmitting information to the implantable stimulator device, wherein the information is configured to program the implantable stimulator device to provide electrical stimulation at the at least two electrodes in accordance with the defined sequence of waveforms.

The GUI may be used to set the change imbalance by selecting a charge imbalance parameter provided by the GUI. The charge imbalance parameter may comprise a difference between the positive phase and the negative phase of the at least one waveform. The difference may comprise a difference in amplitude, a difference in pulse width, or a difference in charge. The difference may be expressed as a ratio, a percentage, or a differential. The GUI may be used to set a charge imbalance between the positive phase and the negative phase of each waveform in the sequence of waveforms.

In the defined sequence of waveforms, a total anodic current sourced to at least one of the at least two electrodes may equal a total cathodic current sunk to at least one of the at least two electrodes at any point in time.

The method may further comprise determining in the external device a pseudo-constant DC current, DC voltage or DC current density to be formed between the at least two electrodes during quiet periods between waveforms in the sequence using at least the charge imbalance. The determined pseudo-constant DC current, DC voltage or DC current density may be displayed using the GUI.

In a fourth example, a system is disclosed, which may comprise: an external device configured to program an implantable stimulator device comprising a plurality of electrodes configured to contact a patient's tissue, wherein the external device comprises control circuitry configured to: generate a graphical user interface (GUI) at the external device; receive, via the GUI, selection of a plurality of parameters defining a sequence of waveforms to be provided to at least two of the electrodes, wherein each waveform comprises a positive phase and a negative phase, wherein one of the parameters comprises of a pseudo-constant DC current, DC voltage or DC current density to be formed between the at least two electrodes during quiet periods between waveforms in the sequence; determine a charge imbalance parameter that adjusts a charge imbalance between the positive phase and the negative phase of at least one waveform in the sequence of waveforms using the plurality of parameters; and transmit information to the implantable stimulator device, wherein the information is configured to program the implantable stimulator device to provide electrical stimulation at the at least two electrodes in accordance with the defined sequence of waveforms as adjusted by the charge imbalance parameter.

In the defined sequence of waveforms as adjusted by the charge imbalance parameter, a total anodic current sourced to at least one of the at least two electrodes may equal a total cathodic current sunk to at least one of the at least two electrodes at any point in time.

The plurality of parameters may comprise at least one of: an amplitude of at least one waveform in the sequence of waveforms, a pulse width of at least one waveform in the sequence of waveforms, a pulse width of the positive phase or the negative phase of at least one waveform in the sequence of sequence of waveforms, or a frequency at which waveforms are provided in the sequence of waveforms.

The control circuitry may be configured to determine the charge imbalance parameter that adjusts the charge imbalance of each waveform in the sequence of waveforms. The control circuitry may be further configured to display the determined charge imbalance parameter in the GUI.

In a fifth example, a non-transitory computer readable media is disclosed which may comprise instructions executable on an external device for programming an implantable stimulator device, wherein the implantable stimulator device comprises a plurality of electrodes configured to contact a patient's tissue, wherein the instructions when executed are configured to enable control circuitry in the external device to: generate a graphical user interface (GUI) at the external device; receive, via the GUI, selection of a plurality of parameters defining a sequence of waveforms to be provided to at least two of the electrodes, wherein each waveform comprises a positive phase and a negative phase, wherein one of the parameters comprises of a pseudo-constant DC current, DC voltage or DC current density to be formed between the at least two electrodes during quiet periods between waveforms in the sequence; and determine a charge imbalance parameter that adjusts a charge imbalance between the positive phase and the negative phase of at least one waveform in the sequence of waveforms using the plurality of parameters.

The instructions when executed may be further configured to enable control circuitry in the external device to: transmit information to the implantable stimulator device, wherein the information is configured to program the implantable stimulator device to provide electrical stimulation at the at least two electrodes in accordance with the defined sequence of waveforms as adjusted by the charge imbalance parameter. The non-transitory computer readable media may further comprise instructions for any of the concepts mentioned in the fourth example.

In a sixth example, a method is disclosed for programming an implantable stimulator device comprising a plurality of electrodes configured to contact a patient's tissue, which method may comprise: using an graphical user interface (GUI) of an external device to define a sequence of waveforms to be provided at at least two of the electrodes, wherein each waveform comprises a positive phase and a negative phase; using the GUI to further specify a pseudo-constant DC current, DC voltage or DC current density that will form between the at least two electrodes during quiet periods between waveforms in the sequence; determine at the external device a charge imbalance parameter that adjusts a charge imbalance between the positive phase and the negative phase of at least one waveform in the sequence of waveforms using at least the pseudo-constant DC current, DC voltage or DC current density; and transmitting information to the implantable stimulator device, wherein the information is configured to program the implantable stimulator device to provide electrical stimulation at the at least two electrodes in accordance with the defined sequence of waveforms as adjusted by the charge imbalance parameter.

The charge imbalance parameter may comprise a difference between the positive phase and the negative phase of the at least one waveform. The difference may comprises a difference in amplitude, a difference in pulse width, or a difference in charge. The difference may be expressed as a ratio, a percentage, or a differential.

In the defined sequence of waveforms as adjusted by the charge imbalance parameter, a total anodic current sourced to at least one of the at least two electrodes may equal a total cathodic current sunk to at least one of the at least two electrodes at any point in time.

The method may further comprise displaying the determined charge imbalance parameter using the GUI. The charge imbalance parameter may be determined using at least one other parameter comprising an amplitude of at least one waveform in the sequence of waveforms, a pulse width of at least one waveform in the sequence of waveforms, a pulse width of the positive phase or the negative phase of at least one waveform in the sequence of sequence of waveforms, or a frequency at which waveforms are provided in the sequence of waveforms.

In all of these examples, the implantable stimulator device may comprise a fully-implantable stimulator device. The implantable stimulator device may also comprise a conductive case, wherein one of the at least two electrodes comprises the conductive case. The implantable stimulator device may also comprise at least one lead that comprises the plurality of electrodes. The implantable stimulator device may also comprise an external stimulator, wherein the plurality of electrodes are implantable in a patient. The implantable stimulator device may also further comprise decoupling capacitors in series with the at least two electrodes. All of these examples may further include the implantable stimulator device itself.

BRIEF DESCRIPTION OF THE DRAWINGS

FIG. 7 shows an example of using charge imbalanced pulses to create Idc in a patient's tissue during quiet periods between the pulses, in which the pulses are pulse width imbalanced.

FIGS. 8A-8E show different examples of charge imbalanced pulses.

FIGS. 15A-15D show charge imbalanced pulses formed using various options provided by the GUI of FIG. 14.

FIG. 16 shows further aspect of the GUI of FIG. 14, and shows a DC algorithm useful to determine or control Idc and related parameters.

DETAILED DESCRIPTION

Figure 1:
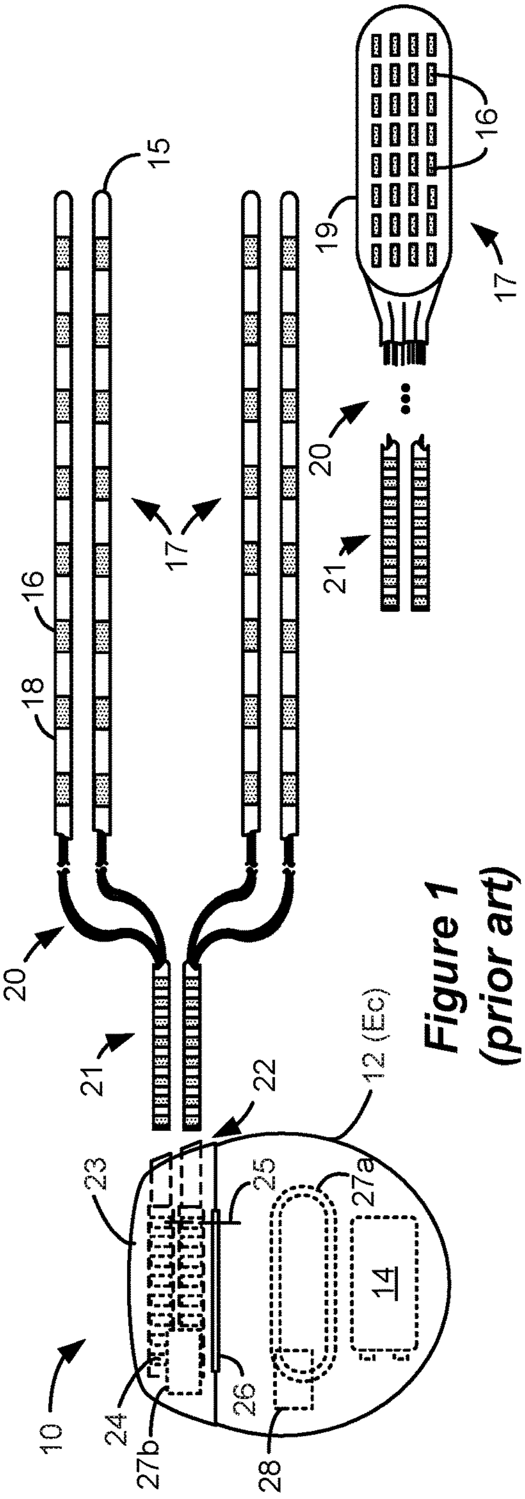
FIG. 1 shows an Implantable Pulse Generator (IPG), in accordance with the prior art.
Figure 2A:
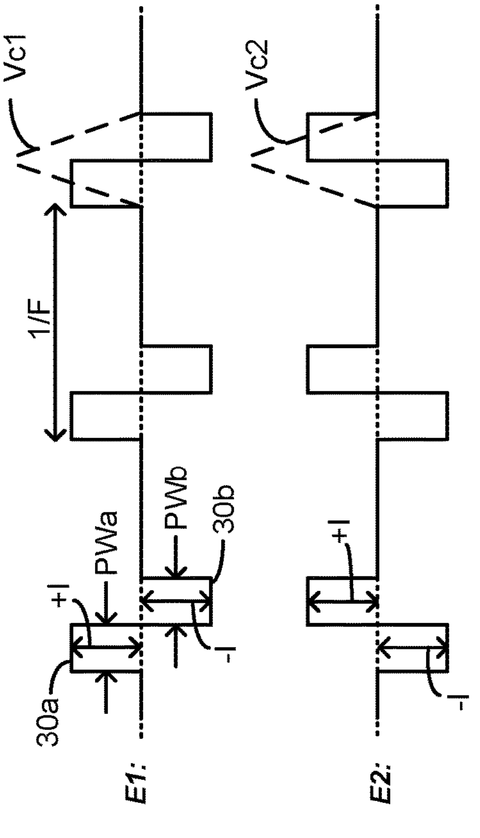
FIGS. 2A and 2B show an example of stimulation pulses (waveforms) producible by the IPG or in an External Trial Stimulator (ETS), in accordance with the prior art.
Figure 2B:
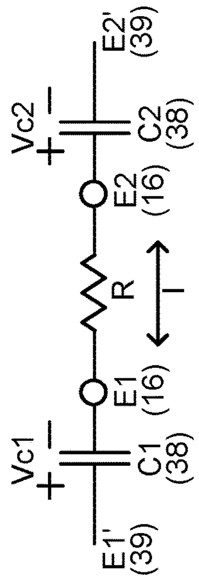
Figure 3:
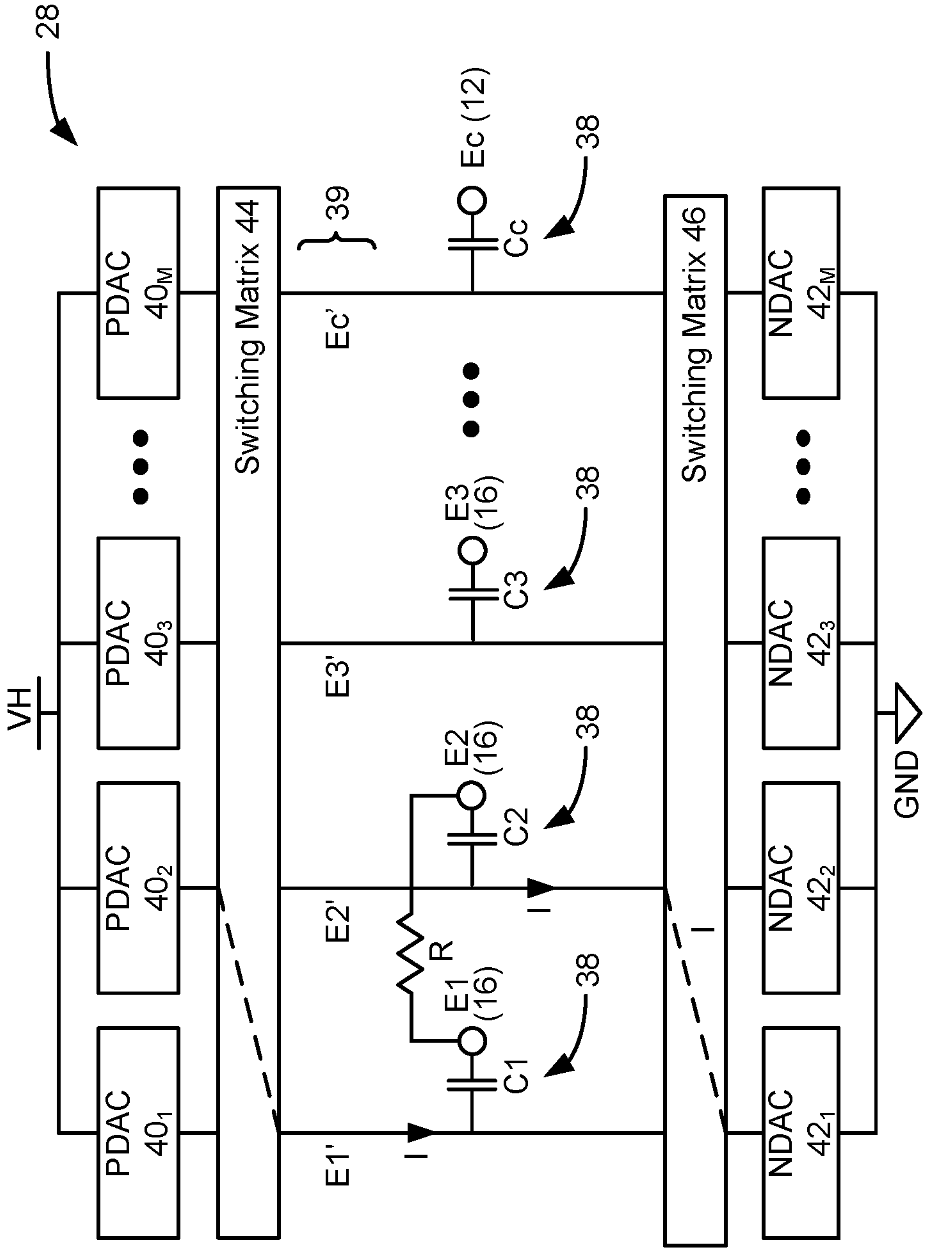
FIG. 3 shows stimulation circuitry useable in the IPG or ETS, in accordance with the prior art.

As discussed in the Introduction, DC-blocking capacitors 38 (FIG. 3) are preferably located in current paths between the electrode nodes 39 and the actual electrodes 16 that contact a patient's tissue. These capacitors 38 provide safety by blocking the flow of DC currents to the tissue, and instead only allow the AC current to pass, such as are provided by time-varying pulses.

Nonetheless, there can be therapeutic benefits to providing a DC current to a patient's tissue. Direct current (DC) current stimulation has emerged as a neuromodulation paradigm having the capability to produce neurologically favorable effects such as symptom relief from neuropsychiatric disorders and neural enhancement. DC current stimulation is also hypothesized to cause specific neurological effects, including but not limited to neuron polarization, changes in synaptic efficacy, or even DC conduction block. See, e.g., M. Bikson et al., "Effects of Uniform Extracellular DC Electric Fields on Excitability in Rat Hippocampal Slices In Vitro," J. Physiology 557.1, pp. 175-190 (2004); A. Rahman et al., "Cellular Effects of Acute Direct Current Stimulation: Somatic and Synaptic Terminal Effects," J. Physiology, 591.10, pp. 2563-2578 (2013); and K. L. Kilgore et al., "Nerve Conduction Block Utilising High-Frequency Alternating Current," Medical & Biological Eng'g & Computing, Vol. 42, pp. 394-406 (2004).

However, the inventors notice problems to implementing DC current stimulation in an IPG or ETS. First, DC current stimulation alone over long periods of time without any AC variation has the potential to erode and corrode the electrodes 16 (typically platinum and/or iridium) used to deliver the stimulation, and can cause tissue damage, especially if current densities exceed about 50 $\mu C/cm^2$ at the surface of the electrode. See, e.g., D. R. Merrill et al., "Electrical Stimulation of Excitable Tissue: Design of Efficacious and Safe Protocols," J. Neuroscience Methods, 141:171-98 (2005); and R. V. Shannon, "A Model of Safe Levels for Electrical Stimulation.," IEEE Trans. on Biomedical Eng'g, Vol. 39, pp. 424-26 (1992).

Second, and as just discussed, DC-blocking capacitors 38 (FIG. 3) are often provided in the current paths of an IPG or ETS. While use of DC-blocking capacitors 38 promotes safety, DC-blocking capacitors inhibit using stimulation circuitry such as 38 to actively drive a DC current because they would block any DC current, or any DC current offset, that the stimulation circuitry 38 might seek to provide.

This is addressed in the present disclosure by providing pulses whose positive and negative phases are not charge balanced. Such charge imbalanced pulses act to charge any capacitances in the current path between electrode nodes selected for stimulation, including the DC-blocking capacitors and/or any inherent capacitances such as those present at the electrode/tissue interface or in the tissue itself. These charged capacitance(s) act during quiet periods between the actively-driven charge imbalanced pulses to induce a pseudo-constant DC current, Idc. Beneficially, these DC currents can be small enough to stay within charge density limits and hence not corrode electrodes or cause tissue damage, and further can be controlled to stay within such limits or for other therapeutic reasons. Graphical user interface (GUI) aspects for generating the charge imbalanced pulses and for determining and/or controlling the pseudo-constant DC current are also disclosed.

Figure 6:
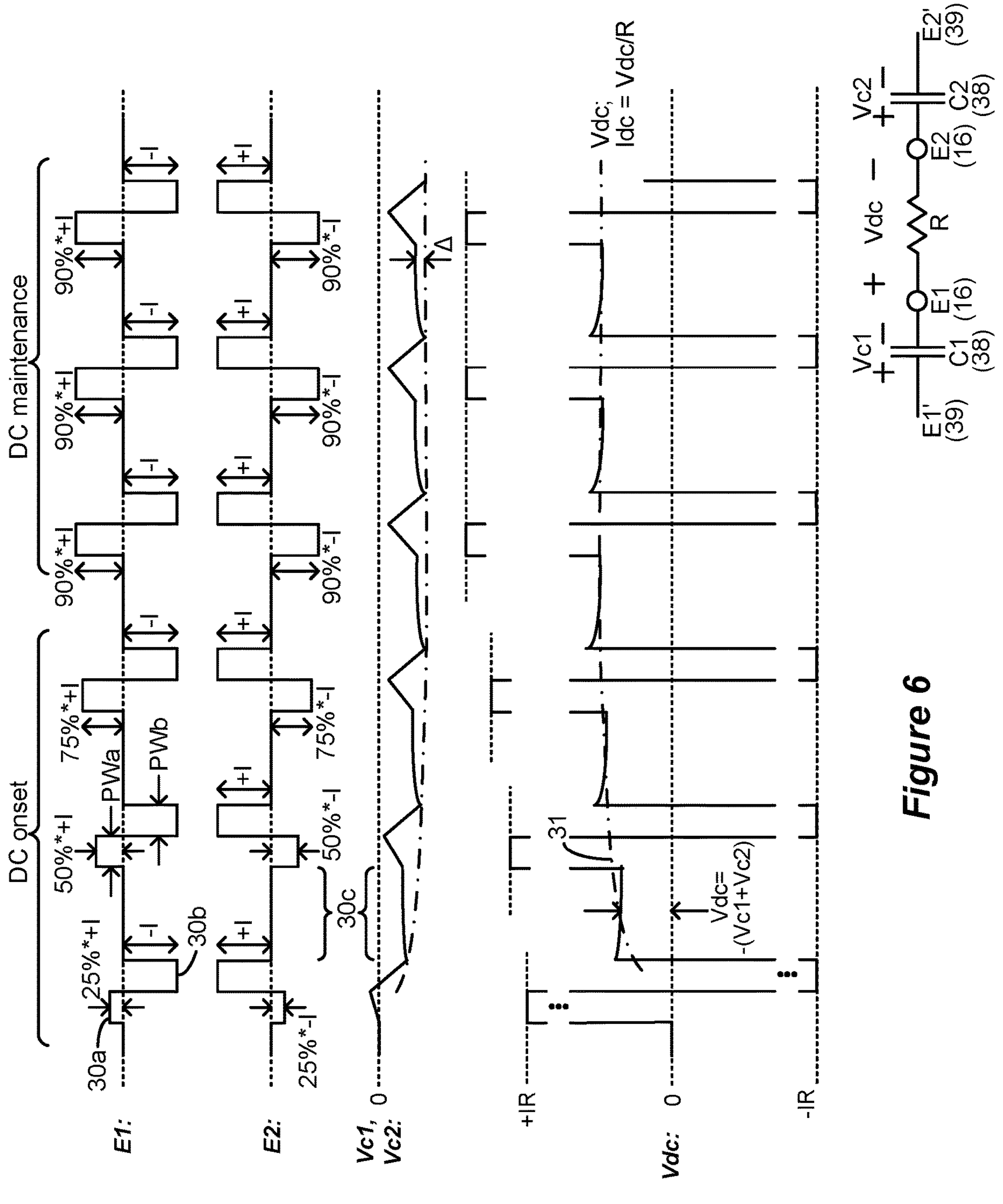
FIG. 6 shows an example of using charge imbalanced pulses to create a pseudo-constant DC current (Idc) in a patient's tissue during quiet periods between the pulses, in which the pulses are amplitude imbalanced.

A first example of the use of charge imbalanced pulses to create a pseudo-constant therapeutic DC current in a patient's tissue is shown in FIG. 6. As will be shown below, this pseudo-constant therapeutic DC current, Idc, will flow from electrode E1 to electrode E2, i.e., the two electrodes selected to provide the stimulation.

In this example, biphasic pulses are used with first and second phases 30*a* and 30*b* of opposite polarities at each of the electrodes. Each pulse is charge imbalanced: for example, the first phase 30*a* of the first pulse at electrode E1 has an amplitude of 25%*+I while its second phase 30*b* has an amplitude of −I. Because the pulse widths of the two phases are equal in this example (PWa=PWb), the total charge of the first pulse phase 30*a* (25%*|+I|*PWa) is 25% of the total charge of the second pulse phase 30*b* (|−I|*PWa). E2 provides the same amplitude of current as does E1 at any point in time, but with opposite polarity so that the total anodic current actively sourced to the tissue equals the total cathodic current sunk from the tissue. Any two or more of the IPG's or ETS's electrodes 16 could be selected to receive charge imbalanced pulses, including case electrode Ec (12). However, E1 and E2 are selected in illustrated examples for simplicity.

In FIG. 6, the amount of charge imbalance of subsequent pulses initially changes over time. The first pulses at E1 and E2 are charge imbalanced at a ratio of 0.25:1 (comparing the first 30*a* and second phases 30*b*), the next at 0.5:1, the next at 0.75:1, then followed by a few pulses with a charge imbalance ratio of 0.9:1. As will be explained further below, the ending pulses (0.9:1) are used to maintain a particular Idc in the tissue R, and are shown as "DC maintenance" pulses. The preceding pulses during which the charge imbalance ramps (from 0.25:1 to 0.9:1) are shown as "DC onset" pulses. It is not necessary to use both DC onset and DC maintenance charge imbalanced pulses, as either could be solely used in the disclosed technique. However, in this example, the DC onset pulses are helpful to more quickly establish Idc, as explained below.

FIG. 6 shows voltages Vc1 and Vc2 that are generated across capacitances present in the current path between electrode nodes E1' to E2' and through the tissue R. These voltages may most significantly comprise the voltages formed across the DC-blocking capacitors 38 that are associated with E1 and E2. However, Vc1 and Vc2 may also include or comprise voltages formed by inherent capacitances in the current path, as explained further below.

Given the manner in which the polarity of Vc1 and Vc2 are defined in FIG. 6, it is seen that both increase slightly during the first phase 30*a* of the first pulse, but then are pulled more strongly negative during the second phase 30*b*. This occurs because the amplitude of the current from E1 to E2 during the first phase 30*a* is smaller than the amplitude of the current in the opposite direction from E2 to E1 during the second phase 30*b*. The rate of increase of Vc1 and Vc2 during the first phase 30*a* is therefore smaller than the rate of decrease of the voltage during the second phase (dV/dt=I/C). The net effect is that at the end of the second phase 30*b*, the capacitances C1 and C2 (assuming they are equal, which isn't necessarily true) are each charged with the same negative voltage Vc1 and Vc2.

During a quiet period 30*c* between the pulses, no active current is being driven by the stimulation circuitry 28/58, i.e., electrode nodes E1' and E2' 39 are disconnected from the stimulation circuitry, as shown at the bottom of FIG. 6. Nonetheless, the previously-charged capacitances will cause a voltage Vdc to be formed across the tissue R from E1 and E2, which given its definition will be opposite the sum of Vc1 and Vc2, i.e., Vdc=−(Vc1+Vc2). Voltages Vc1 and Vc2 will start to exponentially decay towards 0V in accordance with an RC time constant dictated by the capacitances and the resistance R of the tissue, and thus so too will Vdc across the tissue decay. In any event, the creation of Vdc will cause a current Idc to flow from E1 and E2 through the tissue R, where Idc=Vdc/R. Idc, like Vc1, Vc2, and Vdc, will exponentially decay. The extent to which Idc is constant over a quiet period 30*c* will depend on how quickly Vdc is expected to decay based on the RC time constant.

The first DC onset pulse during the DC onset period was significantly imbalanced (0.25:1), which acts to lower Vc1 and Vc2 and raise Vdc/Idc significantly during the subsequent quiet period 30*c*. Subsequent pulses may ramp Vdc/Idc more slowly. Thus, the second pulse in FIG. 6 is not as imbalanced (0.5:1). This charge imbalance continues to pull Vc1 and Vc2 more negative during a next quiet period 30*c*, but not by as much as the first pulse. The result is that Vdc/Idc increases but at a slower rate, as shown by dotted line 31.

Eventually, less-imbalanced DC maintenance pulses (0.9:1) are issued during the DC maintenance period. At this point, the decay Δ in Vc1 and Vc2 during the quiet periods

30*c* equals the variation in Vc1 and Vc2 during the first and second pulse phases 30*a* and 30*b*. Therefore, although Vdc/Idc continues to decay in each quiet period 30*c*, the relative or average value of Vdc/Idc doesn't increase or decrease in the quiet periods 30*c*, and dotted line 31 flatens.

To summarize, through the use of charge imbalanced pulses, capacitances in the current path such as the DC-blocking capacitors 38 and/or capacitances at the electrode/tissue interface or in the tissue become charged, which then produces a current Idc during quiet periods 30*c* between active phases of the pulses such as 30*a* and 30*b*. This is true despite the IPG 10 or ETS 50 having DC-blocking capacitors 38 that would otherwise prevent the stimulation circuitry 28/58 from actively providing a DC current. Therefore, therapeutic benefits of a DC current can be had while still retaining the safety that DC-blocking capacitors 38 provide. Again, the DC current Idc may not perfectly constant during each quiet period 30*c*, and may vary slightly between different quiet periods 30*c*. Nonetheless, Idc is still pseudo-constant, enough so to provide therapeutic benefits such as those described earlier. Further, the magnitude of Idc can be controlled, as explained further below.

FIG. 7 shows another example of charge imbalanced pulses that would have the same effect as the charge imbalanced pulses of FIG. 6 to produce a pseudo-constant current Idc in the tissue. In FIG. 7, charge imbalance is achieved not through amplitude variation but through pulse width variation. Thus, in FIG. 7, all pulse phases 30*a* and 30*b* have the same amplitude—+I or −I depending on the polarity of the phase. However, the pulse widths in phases 30*a* and 30*b* differ. In this example, the pulse width of each second phase 30*b* is set (PWb), but the pulse width of each first phase 30*a* (PWa) comprises a fraction of PWb. Because the charge of each phase comprises its amplitude time its pulse width, this affects the same charge imbalance as occurred in FIG. 6: 0.25:1 for the first pulse, 0.5:1 for the second pulse, and so on. This would similarly charge the capacitances causing Vc1 and Vc2 to decrease during the quiet periods 30*c*, Vdc and Idc to increase, etc. Again, Idc is established in the patient's tissue during the quiet periods 30*c*.

FIGS. 8A-8E show various ways charge imbalanced pulses can be formed to affect the generation of Idc during quiet periods 30*c* as just described. FIGS. 8A and 8B are similar to the pulses shown in FIG. 6 and FIG. 7: FIG. 8A effects charge imbalance by differing the amplitudes of the first and second pulse phases 30*a* and 30*b* while keeping the pulse widths constant; FIG. 8B affects charge imbalance by differing the pulse widths of the first and second pulse phases 30*a* and 30*b* while keeping the amplitudes constant.

FIG. 8C shows that first and second pulse phases 30*a* and 30*b* can be charged imbalanced while being formed of random shapes that are not necessarily square wave current pulses. Charge comprises the integration of current over time (Q=Int (I) d/dt), effectively defining charge as the area under the curve of each phase 30*a* and 30*b*. If these areas are different, charge imbalance is achieved.

FIGS. 8D and 8E show that the first and second phases 30*a* and 30*b* of each pulse can each comprise one or more non-contiguous portions 33*a* and 33*b*. In FIG. 8D, second pulse phase 30*b* comprises different portions 33*b*. Nonetheless, because the charge of pulse portion 30*a* does not equal the sum of the charge provided by portions 33*b* in second pulse phase 30*b*, the pulse is charge imbalanced.

FIG. 8E shows that all portions 33*a* of pulse phase 30*a* need not precede all pulse portions 33*b* of pulse phase 30*b*. In the example shown, the portions 33*a* of positive pulse phase 30*a* are interwoven with the portions 33*b* of negative pulse phase 30*b*. Nonetheless, the sum of the portions 33*a* does not equal the sum of the portions 33*b*, and thus the pulse in total is charge imbalanced.

Figure 9:
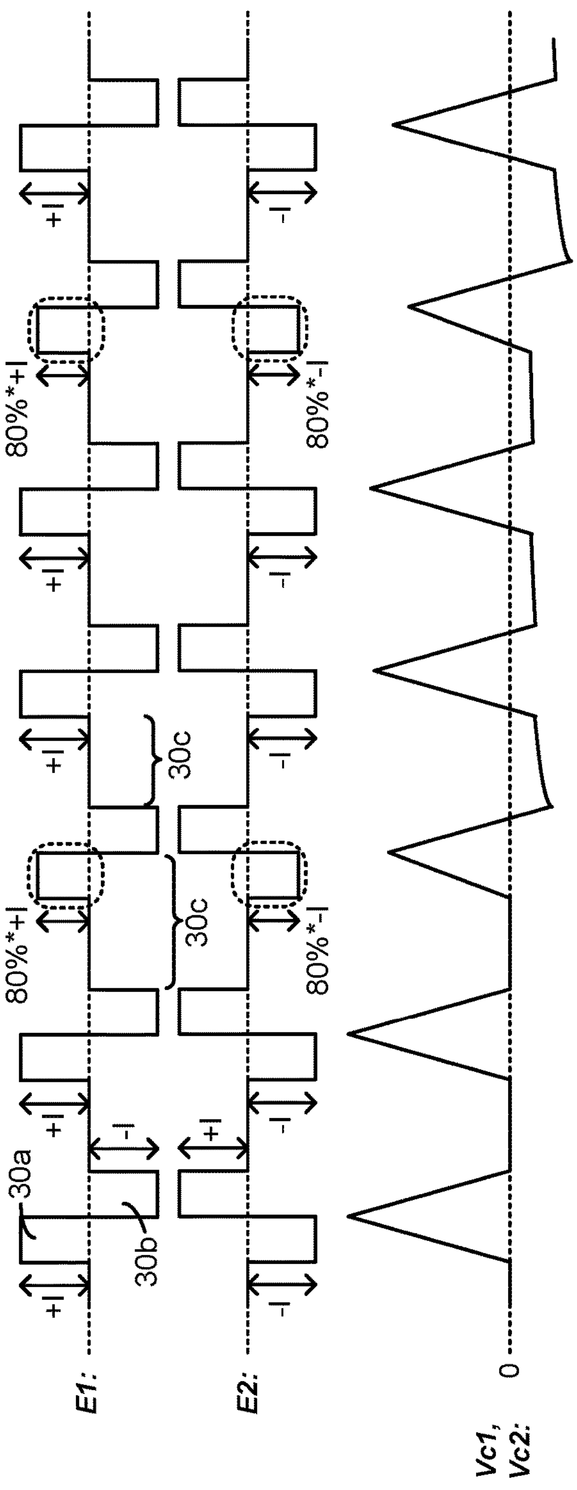
FIG. 9 shows an example of using charge imbalanced pulses to create Idc in a patient's tissue during quiet periods between the pulses, in which only some but not all pulses are charge imbalanced.

FIG. 9 shows that not every pulse need be imbalanced to create Idc in the tissue. In this example, only every third pulse is charge imbalanced: for example, the first two pulses have first and second pulses phases 30*a* and 30*b* each of the same pulse width and amplitude I, which are charge balanced. The third pulse however is charge imbalanced at a ratio of 0.8:1. This would likewise charge any capacitances in the current path, again drawing Vc1 and Vc2 negative during the quiet periods 30*c* after this third pulse. Vc1 and Vc2 are essentially not affected by the next two pulses that are not charge imbalanced, because each of these pulses will increase them during phase 30*a* and decrease them during phase 30*b* by equal amounts. Notice though that Vc1 and Vc2 will still decay during quiet periods 30*c*, until a next charge imbalanced pulse forces Vc1 and Vc2 further negative. The cumulative effect is that Vc1 and Vc2 will decrease over time until the decay of Vc1 and Vc2 equals the amount of charge imbalance provided by the charge imbalanced pulses as explained earlier. At this point Vc1 and Vc2 are essentially constant, and thus so are Vdc and Idc in the tissue R.

Figure 10:
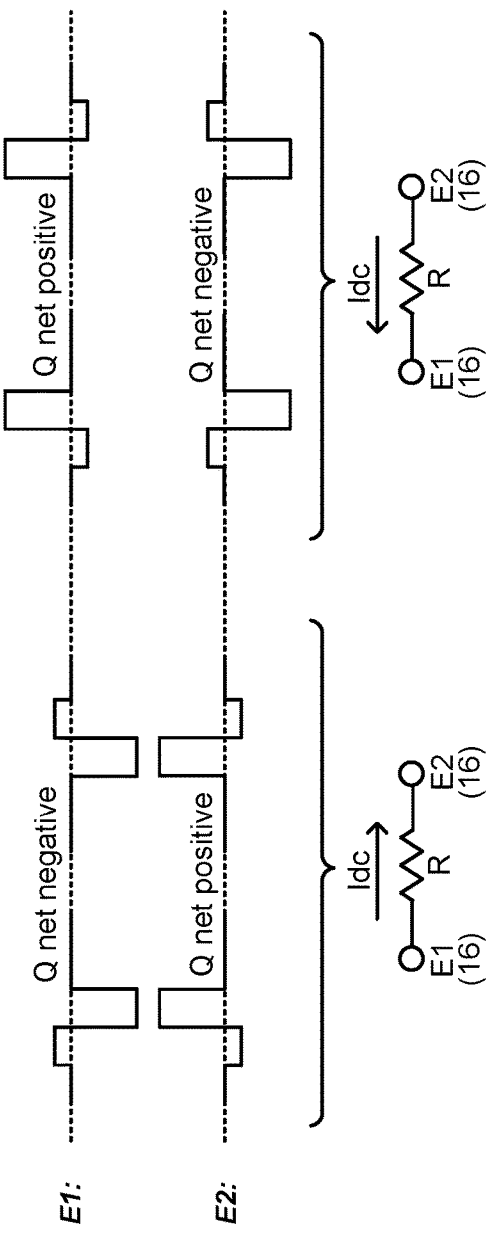
FIG. 10 shows how the charge imbalanced pulses can be manipulated to cause Idc to flow in different directions between selected electrodes.

Idc in the examples shown thus far are made to flow from E1 to E2, because the net charge of the pulses at E1 are negative while the net charge of the pulses at E2 are positive. In this regard, it doesn't matter whether the larger negative pulse phases (or portions) at E1 come before or after the smaller positive pulse phases (or portions), or whether the smaller negative pulse phases (or portions) at E2 come before or after the larger positive pulse phases (or portions), as shown to the left in in FIG. 10. In either case, Vc1 and Vc2 will be drawn negative, thus causing Vdc and Idc to be positive during the quiet periods 30*c*. To reverse the polarity of Vdc/Idc so that it flows from E2 to E1, the polarity of these pulses can be flipped, so that the net charge of the pulses at E1 are positive while the net charge of the pulses at E2 are negative. Again, it doesn't matter whether the larger positive pulse phases (or portions) at E1 come before or after the smaller negative pulse phases (or portions), or whether the smaller positive pulse phases (or portions) at E2 come before or after the larger negative pulse phases (or portions), as shown to the right in FIG. 10. In this circumstance, Vc1 and Vc2 will be drawn positive, thus causing Vdc and Idc to be negative during the quiet periods 30*c*.

Figure 4:
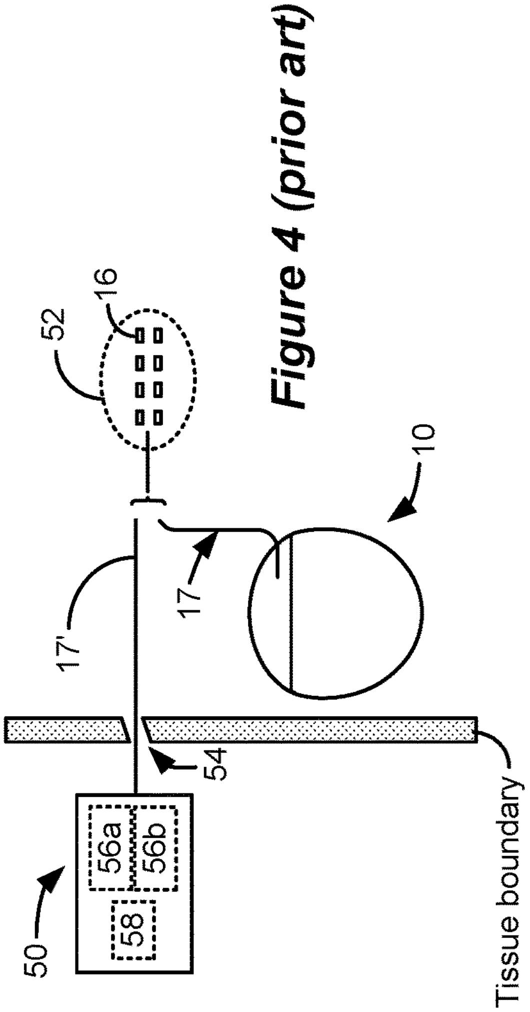
FIG. 4 shows an ETS environment useable to provide stimulation before implantation of an IPG, in accordance with the prior art.
Figure 11:
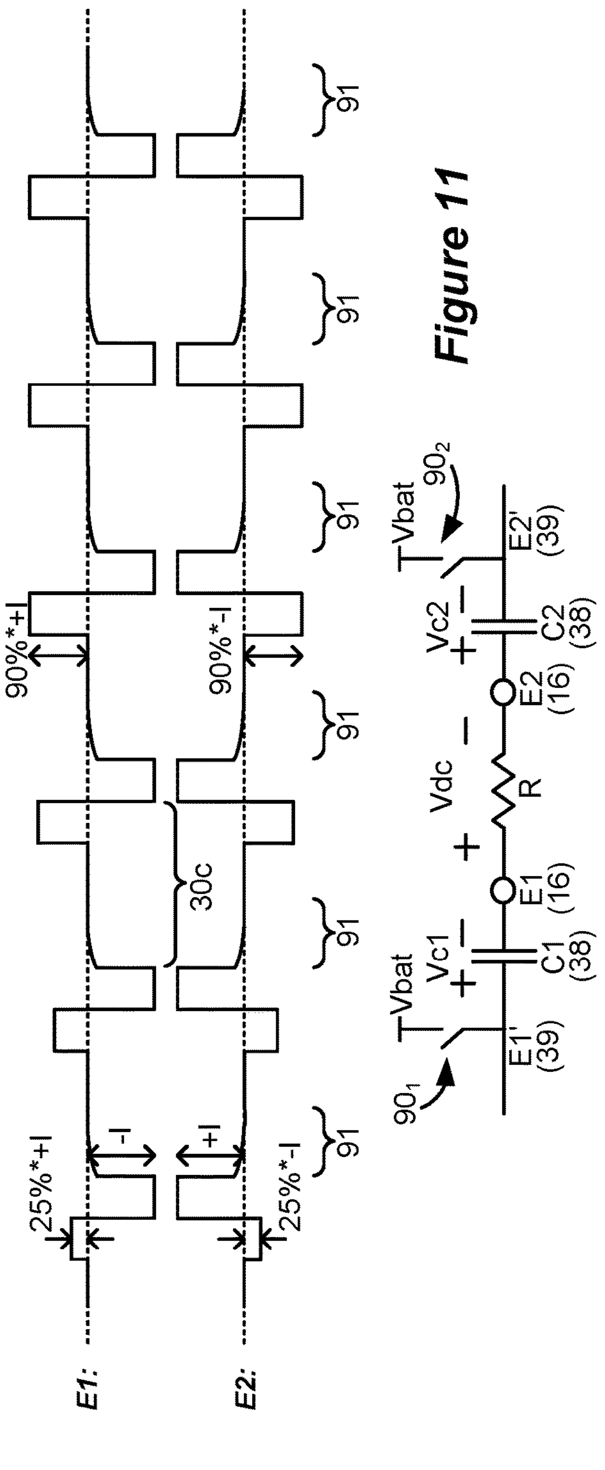
FIG. 11 shows passive charge recovery circuitry that has the potential to interfere with Idc generation, and which can be at least partially disabled.

FIG. 11 illustrates a practical consideration when using charge imbalanced pulses to generate a pseudo-constant DC current Idc in the tissue. Shown are passive recovery switches $\mathbf{90}_i$, which may generally comprise part of the IPG's or ETS's stimulation circuitry 28/58 (FIGS. 3 and 4), and which are described further in U.S. Patent Application Publications 2018/0071527 and 2018/0140831. Passive recovery switches $\mathbf{90}_i$ may be attached to each of the electrode nodes Ei' 39, and are conventionally used to recover any charge remaining on the DC-blocking capacitors Ci 38 after issuance of the active charge recovery pulse 30*b*. Passive charge recovery can be prudent, because active charge recovery using intentionally charge balanced pulse phases 30*a* and 30*b* may not be perfect given non-idealities in the stimulation circuitry. Therefore, passive charge recovery typically occurs after the issuance of second pulse phases 30*b*, for example during the quiet periods 30*c* and more specifically during passive recovery periods 91, by closing passive recovery switches $\mathbf{90}_i$. As explained in the above-cited references, such passive charge recovery tends to equilibrate the charge on the DC-blocking capacitors 38.

However, when intentionally using charge imbalanced pulses to generate a pseudo-constant DC current Idc in the tissue in accordance with the disclose technique, it may be desirable to disable passive charge recovery, i.e., to disable closing of the passive recovery switches 90$_i$ entirely or for at least a portion of the passive recovery periods 91. This is because the disclosed technique intentionally charges the DC-blocking capacitors 38 (or other charging path capacitances) as a means to generate Idc, whereas passive charge recovery seeks to remove such charged capacitances. However, as passive charge recovery may also promote the flow of current through the tissue in some circumstances, it is not strictly necessary that passive charge recovery be disabled when generating Idc.

Figure 12:
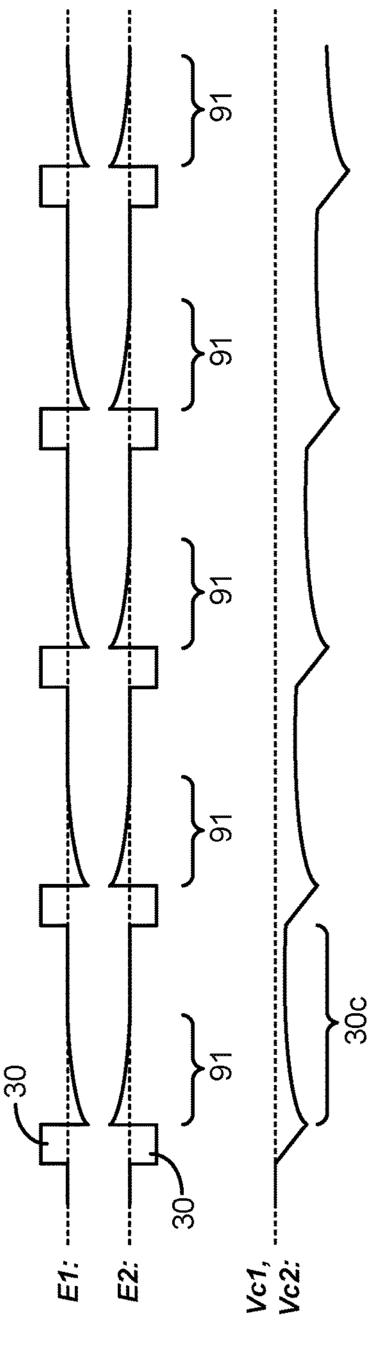
FIG. 12 shows monophasic charge imbalanced pulses useable to generate Idc in a patient's tissue.

FIG. 12 shows that the disclosed technique need not involve the use of biphasic pulses with positive and negative pulse phases. Instead, as shown, monophasic pulses can be used having only a single pulse phase 30. Such monophasic pulses have a net charge and are therefore inherently charge imbalanced, and so will charge the DC-blocking capacitors 38, causing Vc1 and Vc2 to drop as shown. The charged capacitances will again decay during quiet periods 30*c*, and if they don't decay back to Vc1=Vc2=0, then a subsequent pulse phase 30 will drive Vc1 and Vc2 even further negative. As before, this would continue (if not controlled, as discussed shortly) until the decay equals the total charge of the pulses, at which point Vdc and Idc would stop rising during each subsequent quiet period 30*c*.

Traditionally, monophasic pulses 30 such as those shown in FIG. 12 are followed by a passive recovery period 91, as explained with reference to FIG. 11, to passively recover any charge stored on capacitances in the current path. Thus, it may again be desirable to disable closing of the passive recovery switches 90$_i$ for all or a portion of the passive recovery periods 91 so as not to defeat the mechanism by which Idc is generated.

Figure 13:
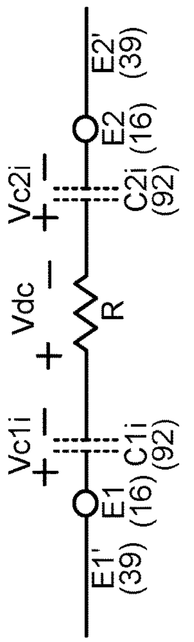
FIG. 13 shows the use of inherent capacitance in the current path between active electrodes useful in generating Idc.

The disclosed technique is particularly well suited to use in IPG or ETS having DC-blocking capacitors 38 because, as discussed above, it provides a means of providing a pseudo-constant DC current even though the DC-blocking capacitors 38 act to prevent DC current from being driven by the stimulation circuitry 28/58 into the tissue. However, the disclosed technique is not limited to use in IPGs or ETSs having DC-blocking capacitors 38, as shown in FIG. 13. In FIG. 13, DC-blocking capacitors 38 are not present in the current path. However, inherent capacitances C1*i* and C2*i* 92 are shown, which comprise any inherent capacitance in the current path. In particular, inherent capacitances 92 may comprise the capacitances naturally present at the electrode 16/tissue R interfaces. Inherent capacitances 92 could also comprise capacitances naturally present in the tissue R itself, which can be modeled as a single capacitance. In any event, the inherent capacitance(s) 92 can also be charged by the charge imbalanced pulses and used to provide Idc as described.

Figure 5:
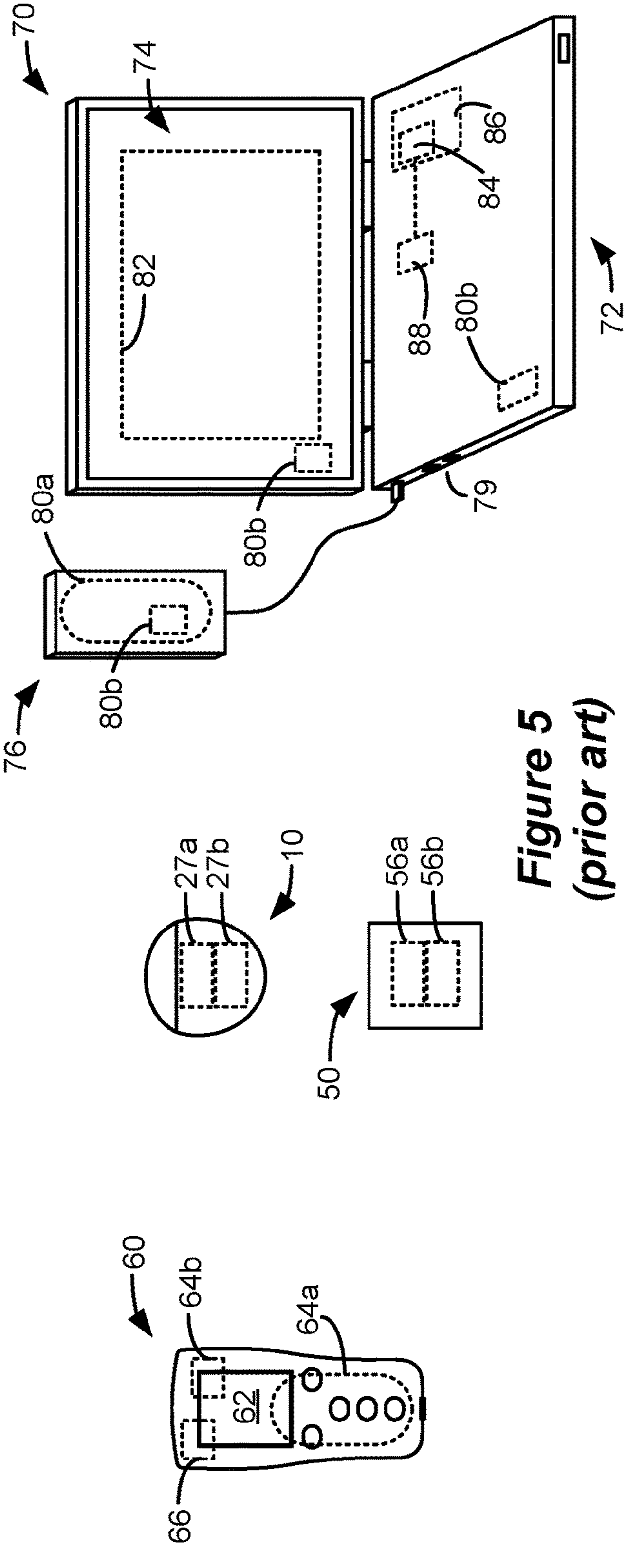
FIG. 5 shows various external devices capable of communicating with and programming stimulation in an IPG and ETS, in accordance with the prior art.
Figure 14:
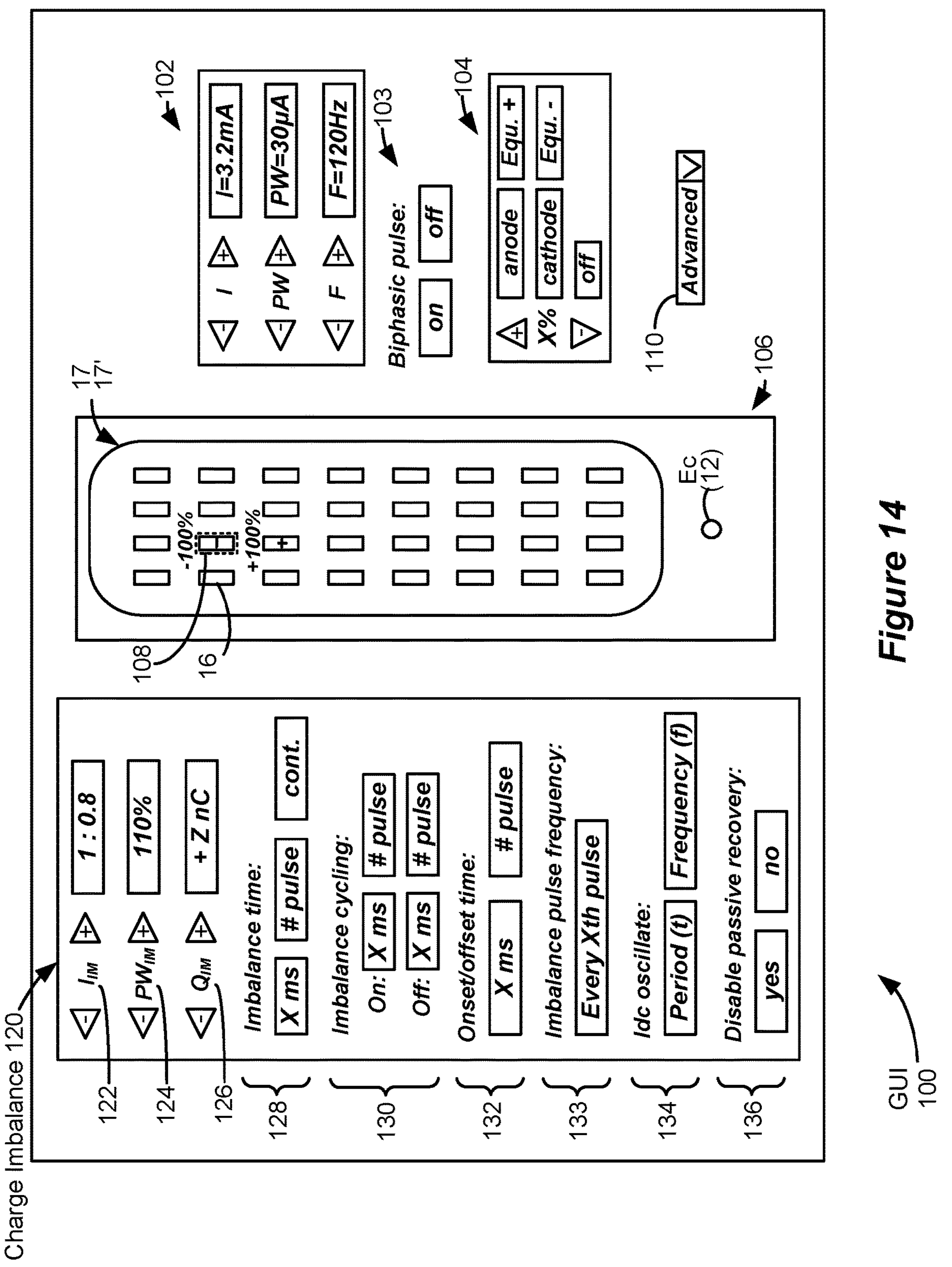
FIG. 14 shows a Graphical User Interface (GUI) operable in an external device and useable to define charge imbalanced pulses to create and control Idc in a patient's tissue during quiet periods between the pulses.

A portion of a Graphical User Interface (GUI) 100 useable to define charge imbalanced pulses and to control the generation of Idc in patent tissue is shown in FIG. 14. GUI 100 preferably runs in an external device as described earlier and can telemeter stimulation parameters to the IPG 10 or ETS 50 for execution. In the description that follows it is assumed for simplicity that GUI 100 is executed on a clinician programmer 70 (FIG. 5) as part of its clinician programmer software 84 and as executable in its control circuitry 88, as described earlier. However, GUI 100 can also similarly be executed on an external controller 60 (FIG. 5). GUI 100 may comprise a portion of module of a more general GUI running of the clinician programmer 70, such as GUI 82 (FIG. 5). GUI 100 may be presented to the user based on where the clinician programmer software 84 is in its execution, which may depend on GUI selections the clinician has previously made. GUI 100 need not comprise just a single displayed screen, but can include multiple screens that are presented based on user selections.

GUI 100 can provide options to set stimulation parameters for the patient. For example, values for stimulation parameters such as amplitude (I), pulse width (PW), and frequency (F) can be displayed and set in a waveform parameter interface 102, including buttons the clinician can use to increase or decrease these values. Amplitude I sets the value of the total anodic current +I one or more selected anode electrodes will source to the patient, and the value of the total cathodic current −I one or more selected anode electrodes will sink from the patient. Pulse width PW can allow a total duration of pulses to be set, or may set the pulse widths of the pulse phases (such as PWa and PWb) individually, although this isn't shown for simplicity. Option 103 allows the user to choose whether the pulses are to be applied as biphasic pulses or not. If biphasic pulses are selected, the information entered in waveform parameter interface 102 can be automatically applied to both the first 30*a* and second 30*b* phases of the pulse. In the description that follows, it is assumed that biphasic pulses have been selected.

Stimulation parameters relating to the electrodes 16 are made adjustable in an electrode parameter interface 104. Electrodes are manually selectable in a leads interface 106 that displays a graphical representation of the electrode array 17 or 17' that has been implanted in a particular patient (a paddle lead 19 is shown as one example). A cursor 108 or other selection means such as a mouse pointer can be used to select a particular electrode in the leads interface 106. Buttons in the electrode parameter interface 104 allow the selected electrode (including the case electrode, Ec) to be designated as an anode or cathode (during first pulse phases 30*a*), or off. The electrode parameter interface 104 further allows the relative amount of total anodic or cathodic current +I or −I of the selected electrode to be specified in terms of a percentage, X. This is particularly useful if more than one electrode is to act as an anode or cathode at a given time. In the example shown, two electrodes have been selected, one as an anode (+) which will receive 100% of the total anodic current +I, and another as a cathode (−) which will receive 100% of the total cathodic current −I.

More automated means can be used to choose electrodes for stimulation. In U.S. Pat. No. 8,412,345 for example, target poles can be chosen in a GUI and may not correspond to the locations of physical electrodes 16. Target poles are then processed by the clinician programmer software 84 to determine which physical electrodes 16 should be selected, and with what relative amplitudes and polarities, to best approximate the desired electric field in the tissue as defined by the target poles.

An advanced menu 110 can be used (among other things) to define more complicated pulses or waveforms more generically. For example, advanced menu 110 can be used to set specific amplitudes (I) and pulse widths (PW) of individual phases of a pulse, to set pulse phases with random shapes (FIG. 8C), or to set pulses whose phases comprise portions 33*a* and 33*b* if applicable (FIGS. 8D and 8E), although these details aren't shown. Advanced menu 110 can also allow for the selection of more advanced modifications to the waveforms, such as setting of a duty cycle (on/off time) for the waveforms, a ramp-up time over which the waveforms reach the programmed amplitude (I), various parameters relating to the issuance of a burst of waveforms, parameters relevant to defining waveforms of random (e.g., non-constant pulse) shapes, etc.

GUI 100 also includes a charge imbalance interface 120 which allows a user to select one or more charge imbalance parameters to modify the pulses as otherwise prescribed (e.g., using interfaces 102 and 104), and hence generate Idc in the tissue.

For example, option 122 allows a charge imbalance parameter $I_{IM}$ to be set for the first and second pulses phases 30*a* and 30*b* (or their portions 33*a* and 33*b*; see FIGS. 8D and 8E), which describes a difference in the amplitude of the current that will be applied during each phase. This amplitude imbalance parameter $I_{IM}$ can be specified in different manners. In FIG. 14, $I_{IM}$ is shown as a ratio (X:Y), with X specifying the amplitude of the first phase 30*a*, and Y specifying the amplitude of the second phase 30*b*. Thus, 1:0.8 would mean that the first phase 30*a* would receive an amplitude of I, while the second phase 30*b* would receive an amplitude of 0.8*I, with their polarities being set at the selected electrodes in accordance with their status as anodes or cathodes. Amplitude imbalance parameter $I_{IM}$ can also be specified as a percentage; for example, 125% would equal 1/0.8. A differential percentage could also be used; for example 1/0.8 could be represented as −20%. Amplitude imbalance parameter $I_{IM}$ can also be specified by a charge differential between the two phases (e.g., in nC), which is computable by multiplying the amplitude of each phase times its pulse width (or the sum of the widths of its portions). If the first phase 30*a* is to have a smaller charge than the second phase 30*b*, the ratio can be smaller than 1 (e.g., 0.8:1), the percentage can be less than 100% (e.g., 80%), the differential percentage can be positive (+20%) or the charge differential can be negative (e.g., −10 nC). Amplitude imbalance parameter can also comprise the strength of the weaker phase relative to the stronger phase or vice versa using any of these metrics.

Use of amplitude imbalance parameter $I_{IM}$ to set a desired charge imbalance may be most useful if the first and second pulses phases 30*a* and 30*b* have constant amplitudes and equal pulse widths PWa and PWb (see, e.g., FIG. 8A), although $I_{IM}$ is not so limited.

Other charge imbalance parameters can also be used. Option 124 allows a charge imbalance parameter $PW_{IM}$ to be set for the first and second pulses phases 30*a* and 30*b* (or their portions 33*a* and 33*b*), which describes a difference in the pulse width that will be applied during each phase. In FIG. 14, a percentage is shown, but again a ratio, charge differential, or other metric could be specified. Use of pulse width imbalance parameter $PW_{IM}$ to set a desired charge imbalance may be most useful if the first and second pulses phases 30*a* and 30*b* have equal constant amplitudes (see, e.g., FIG. 8B), although again $PW_{IM}$ is not so limited.

Option 126 allows a charge imbalance parameter $Q_{IM}$ to be set for the first and second pulses phases 30*a* and 30*b* (or their portions 33*a* and 33*b*; see FIGS. 8D and 8E), which describes a difference in the total charge that will be applied during each phase. Again, a ratio, percentage, or other metric could also be specified for $Q_{IM}$. Use of charge imbalance parameter $Q_{IM}$ to set a desired charge imbalance may be most useful if the first and second pulses phases 30*a* and 30*b* have unusual or randomized shapes (see, e.g., FIG. 8C), but again $Q_{IM}$ is not so limited.

Note that charge imbalance parameter options 122-126 used to select a charge imbalance parameter may be made on a per electrode basis, for example, the electrode currently selected by cursor 108. This can be important to control the direction that Idc will flow. For example, if electrode E1 is an anode (during its first phase 30*a*), and it is desired that Idc flow from E1 to E2 (see FIG. 10), then options 122-126 should reflect that first phase 30*a* will have a smaller amount of charge than second phase 30*b*.

Figures 15A, 15B, 15C:
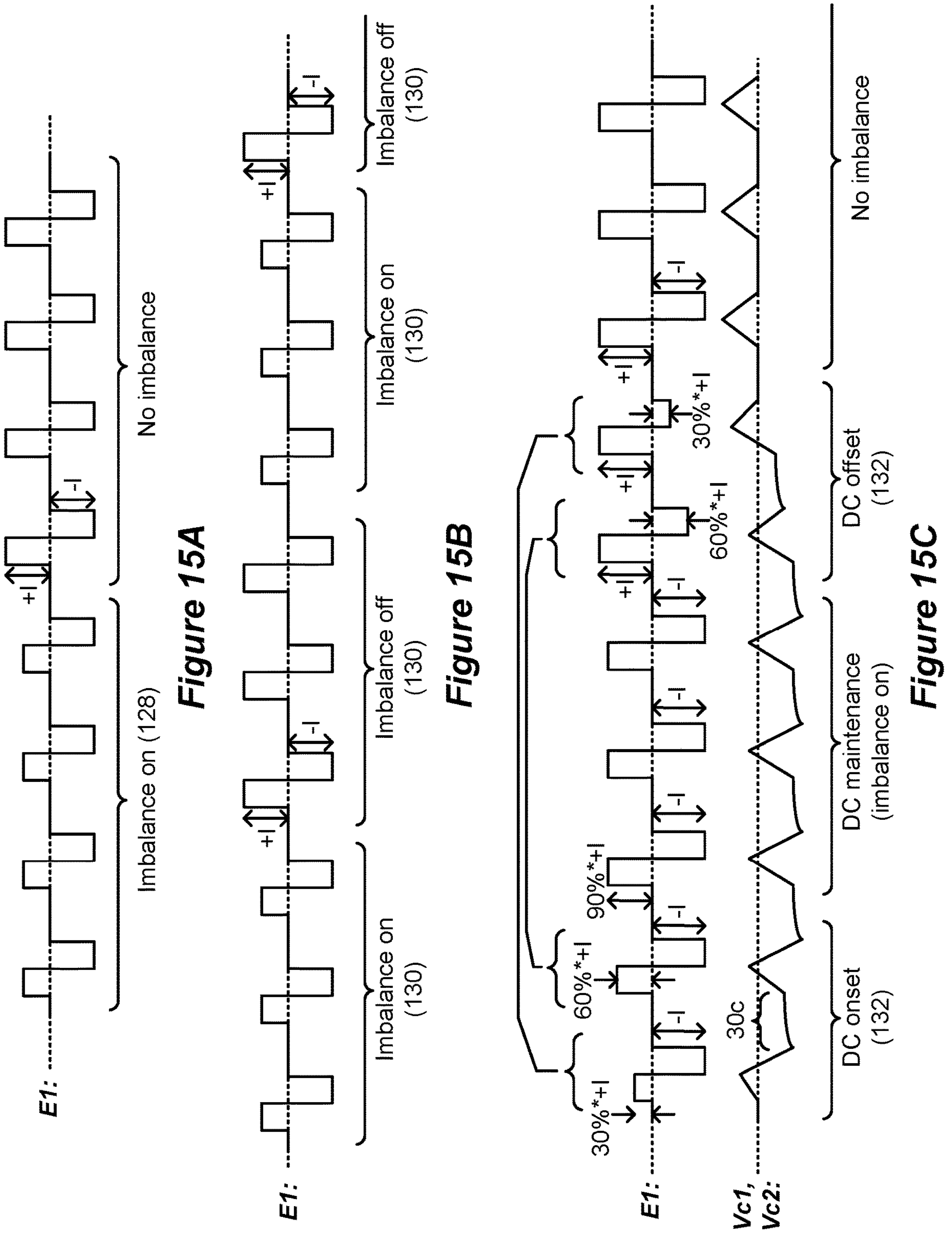

Other options in the charge imbalance interface 120 specify manners in which the charge imbalance parameter (e.g., $I_{IM}$, $PW_{IM}$, $Q_{IM}$) can be applied to a sequence of pulses or waveforms more generally. For example, option 128 in the charge imbalance interface 120 can be used to set a period over which the charge imbalanced pulses are issued, as shown in FIG. 15A for electrode E1 only, although electrode E2 would be of opposite polarity as before. The charge imbalance period can be specified as a time period, or as a number of pulses, or in other manners. This can be useful for example if it is desired to test charge imbalanced pulses and generate Idc in a patient for just a set period of time. Alternatively, option 128 may also include an option to allow the charge imbalanced pulses to issue continuously ("cont.") for an indefinite time period.

Option 130 allows imbalanced pulses to be cycled on and off for different time periods, as shown in FIG. 15B. This can include options to specify an "on" time or number of pulses that charge imbalanced pulses will issue, and an "off" time or number of pulses that non-charge imbalanced pulses will issue. These on and off periods are then cycled so that Idc is formed in the tissue during the on periods, but not during the off periods.

Option 132 in the charge imbalance interface 120 can be used to set the DC onset during which the charge imbalance in the pulses is ramped to a desired amount, as explained earlier with reference to FIG. 6, but shown again in FIG. 15C. The DC onset can be specified as a time period, or as a number of pulses over which the charge imbalance is ramped (just two ramped pulses with ratios of 0.3:1 and 0.6:1 are shown in FIG. 15C). The clinician programmer software 84 can automatically compute the amount of charge imbalance during specified ramping periods, such as by scaling the charge imbalance during the ramp, which scaling can be linear, exponential, or generally non-linearly. The DC onset period can be followed by non-ramped charge imbalanced pulses (e.g., 0.9:1), such as the DC maintenance period described earlier (FIG. 6), or the "imbalance on" time periods of FIGS. 15A and 15B.

Note also that option 132 can comprise a DC offset time during which charge imbalance is ramped downward. This is helpful to ramp Idc back to zero as explained in FIG. 15C. Notice that two ramp down pulses are used, which mirror the two ramp up pulses, but have their polarities changed. For example, whereas the first ramp up pulse has a ratio (plus to minus) of 0.3:1 to accelerate pulling Vc1 and Vc2 negative (and thus Vdc and Idc positive), the last ramp down pulse has a ratio of 1:0.3 to accelerate pulling Vc1 and Vc2 (and thus Vdc and Idc) positive and back to zero. Again, the clinician programmer software 84 can automatically define the magnitudes and phases of the DC offset pulses over the specified time period. Although not shown in FIG. 14, option 132 can include the ability to separately control the DC onset and DC offset times, as they don't need to be equal.

Option 133 allows Idc to be generated by specifying how frequently charge imbalanced pulses are issued. For example, and similar to what was shown earlier in FIG. 9, option 133 can be used to specify that every third pulse can be charge imbalanced, with remaining pulses being charge balanced. More complicated manners for specifying how to intersperse charge imbalanced and charge balanced pulses can also be specified at option 133, allowing more complicated patterns to be defined.

Option 134 allows the Idc to be controlled so that it oscillates between positive and negative. In other words, Idc will flow from E1 to electrode E2 during some periods, and will flow in the opposite direction from E2 to E1 during other periods. This is shown in FIG. 15D, which shows charge imbalanced pulses being formed in alternating periods 135*a* and 135*b*. During periods 135*a*, the pulse at E1 have a net negative charge, which as explained earlier with reference to FIG. 10, causes Idc to flow from E1 to E2. During periods 135*b*, the pulses at E1 have a net positive charge, which can occur for example by reversing the charge imbalance ratio of the pulses. For example, while the charge imbalance ratio of the pulses at E1 in periods 135*a* is 0.5:1, the ratio is 1:0.5 in periods 135*b*. Using such net positive pulses in periods 135*b* causes Idc to flow in the opposite direction from E2 to E1. Thus, Idc will oscillate over a period t, or with a frequency f, as shown in FIG. 15D. Option 134 can provide options to allow this period or frequency to be set as shown in FIG. 14, or Idc oscillation can be specified by other means, such as by defining the duration of periods 135*a* and 135*b*. Note that the transition in the polarity of Idc may not be sharp at the boundary between the periods 135*a* and 135*b*, as it may take some time for net positive charge pulses to offset Vc1 and Vc2 charging caused by preceding net negative charge pulses, and vice versa. Nonetheless, Idc's polarity can generally be made to oscillate.

The charge imbalance interface 120 in FIG. 14 can also include an option 136 to control passive charge recovery during periods when charge imbalanced pulses are issued. As explained earlier with reference to FIG. 11, passive charge recovery during the quiet periods 30*c*—i.e., turning on passive recovery switches $\mathbf{90}_i$ during recovery periods 91—can interfere with building charge on the capacitances, which can interfere with Idc generation. Thus, option 136 provides the ability to disable passive charge recovery when charge imbalanced pulses are issued. Although not shown, further control could allow passive recovery to be limited to some degree rather than being completely disabled.

Changes to therapy made within GUI 100, including changes pertaining to prescribing charge imbalanced pulses as just described, can be compiled as a stimulation program by the control circuitry 88 and wirelessly transmitted by the clinician programmer 70's antenna 80*a* and/or 80*b* (FIG. 5) and its telemetry circuitry to the IPG 10 or ETS 50 for execution by their stimulation circuitries 28 and 58, as explained earlier.

FIG. 16 shows further options in the charge balance interface 120 that can be used to estimate or control Vdc, Idc, or Jdc in accordance with a DC algorithm 150 operable as part of clinician programmer software 84 and executable in control circuitry 88 (FIG. 5). Instructions for DC algorithm 150 and for GUI 100 more generally can be stored on a non-transitory computer readable media, such as a solid state, optical, or magnetic memory residing in or associated with the control circuitry 88. The algorithms can also be stored on similar media outside the external device, such as on an (Internet) server or an external memory stick or disk, and loaded into the relevant external device.

Jdc comprises the current density of Idc at the selected electrodes, which generally varies as a function of the area A of the electrodes 16 and Idc. For example, Jdc may generally comprise Idc/A, and is written as such in FIG. 16 for simplicity. However, Jdc may also comprise a maximum value as determined from Idc and A, but also based upon modelling that takes into account the shape of the electrodes. In this regard, the current density may not be uniform across the entire area of the electrodes 16. For example, the current density may be maximized at the edges of the electrodes, and therefore Jdc may comprise this maximum current density. The electrode area A and any modelling useful for calculating a maximum current density can be programmed into the DC algorithm 150, although this isn't shown.

As explained earlier Vdc=Idc/R, where R is the resistance of the patient's tissue between the selected electrodes. Techniques for measuring R in an IPG or ETS are well known. See, e.g., U.S. Pat. No. 9,061,140 (describing a technique for measuring R). Thus, R can be measured by the IPG or ETS, transmitted to the clinician programmer 70, and programmed into or stored in the control circuitry for use by the DC algorithm 150.

The Idc algorithm 150 can preferably both (i) determine a pseudo-constant Vdc, Idc, and/or Jdc using set stimulation parameters and one or more charge imbalance parameters, and/or (ii) determine one or more charge imbalance parameters using a set Vdc, Idc, and/or Jdc and stimulation parameters.

Indicators 140 show estimations of Vdc, Idc, and/or Jdc for a specified waveform having charge imbalanced pulses. To provide these estimations to the user of GUI 100, the DC algorithm 150 can receive and process various pieces of information at a modeling logic block 152. For example, modeling block 152 can receive one or more of the parameters specified in the GUI 100 of FIG. 14. Such parameters can comprise stimulation parameters that do not promote charge imbalance, such as the amplitude I, pulse width(s) PW, and frequency F as specified in waveform parameter interface 102. Modeling block 152 also preferably receives one or more parameters relevant to how the waveform is charge imbalanced, such as the amplitude imbalance, pulse width imbalance, or charge imbalance 122-126 ($I_{IM}$, $PW_{IM}$, $Q_{IM}$). Although not shown in FIG. 16, modeling block 152 may further receive other parameters relevant to charge imbalancing such as the imbalance time 128, imbalance cycling 130, onset/offset time 132, imbalance pulse frequency, Idc oscillation parameters 134, and whether passive recovery is disabled 136.

Modeling block 152 may also receive the resistance of the tissue R between the selected electrodes, which as pointed out earlier can be measured at the IPG 10 or ETS 50 and stored in a manner accessible by the control circuitry 88 in the clinician programmer 70. Modeling block 152 may also receive information regarding one or more capacitances in the current path between the selected electrodes C, such as the capacitance of the DC-blocking capacitors 38 C1 and C2, and any other inherent capacitances. The values of such capacitances if already known can be stored, or may be determined by a telemetered measurement in the IPG 10 or ETS 50. For example, a measurement voltage Vm across the electrodes nodes 39 E1' and E2' may be measured, which spans across capacitances in the current path. The capacitance can be determined by monitoring the rate at which Vm changes in response to a known constant current (i.e., I=C dVm/dt). Finally, modeling block 152 may include information regarding the electrode areas A, which again may be stored.

From one or more of these pieces of information, the modeling block 152 can determine Vdc, Idc (Vdc/R), and Jdc (a function of Idc, A, and perhaps electrode geometry modelling as explained above). This can occur by using a look up table 154 which correlates the various parameters to one or more of Vdc, Idc, or Jdc. For example, look up table 154 may reveal that for 30 specified biphasic pulses with stimulation parameters such as an amplitude I=2 mA, a pulse width of PW=30 microseconds, and a frequency of F=100 Hz, and with a charge imbalance parameter such as an amplitude imbalance ratio $I_{IM}$ of 0.8:1, and assuming a capacitance of values C1 and C2, Vdc will equal 100 mV, or may be within a range of 50 to 200 mV, either of which may then be indicated at 140. Idc and Jdc may then also be indicated at 140 using R and A as explained above. The data in look up table 154 may be established using mathematical relationships or based on actual empirical or experimental data.

Option 144 in charge imbalance interface 120 may be used to set limits for Vdc ($Vdc_{MAX}$), Idc ($Idc_{MAX}$), and/or Jdc ($Jdc_{MAX}$). Such maximum limits can be adjustable by the user, or may comprise non-adjustable limits set in the clinician programmer software 84. This can be important particularly as concerns $Jdc_{MAX}$, because, as pointed out earlier, exceeding DC current density limits for extended periods of time can corrode electrodes or cause tissue damage. If the determined Vdc, Idc, or Jdc exceeds the maximum limit specified at option 144, the DC algorithm 150 can issue an alarm. In one example not shown, GUI 100 can display a message on the screen 74 of the clinician programmer 70 alerting the user to the fact that the parameters entered will exceed one or more of $Vdc_{MAX}$, $Idc_{MAX}$, or $Jdc_{MAX}$. The user of GUI 100 may decide to override these maximum limits, or alternatively the clinician programmer software 84 may (for safety) reject the charge imbalance parameters that lead to these limits being exceeded. For example, the GUI 100 may either automatically adjust relevant charge imbalance parameters (such as $I_{IM}$) so that no maximum limit is exceeded, or may prevent transmission of these charge imbalance parameters to the IPG 10 or ETS 50. An alarm may be implemented in other manners.

The DC algorithm 150 may also allow a user to set a particular value or range for Vdc, Idc, or Jdc using option 142. When one of these values is set using option 142, the DC algorithm 150 will preferably automatically set one or more charge imbalance parameters appropriately in the GUI 100 to achieve the set value. (Stimulation parameters could also be automatically adjusted or set, but this is less preferred). Such adjustment can essentially work the reverse of the process just described. For example, if the user inputs at option 142 specify that Idc should equal 30 μA, DC algorithm 150 can equate this value (using R) to Vdc=100 mV (Vdc=Idc*R). Using the look up table 154 in the modeling block 152, the DC algorithm 150 can determine the relevant charge imbalance parameter (e.g., 122-126, perhaps as modified by 128-136) necessary to achieve the desired Vdc=100 mV. This may depend on the stimulation parameters (e.g., I, PW, F) otherwise chosen. Given such stimulation parameters, the DC algorithm 150 may for example conclude that amplitude imbalance $I_{IM}$ should be set to 0.85:1, and thus may automatically populate option 122 accordingly. Options 124 (pulse width imbalance $PW_{IM}$) or 126 (charge differential $Q_{IM}$) could likewise or additionally be so populated. DC algorithm 150 may additionally recognize that other charge imbalance parameters would be useful to automatically select. For example, DC algorithm 150 might determine that to create the desired Vdc, Idc, or Jdc set at option 142, imbalance may need to be cycled (option 130), and may automatically populate this option.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A system, comprising:

an external device configured to program an implantable stimulator device comprising a plurality of electrodes configured to contact a patient's tissue, wherein the external device comprises control circuitry configured to:

receive a plurality of parameters defining a waveform, wherein the waveform comprises a positive phase and a negative phase;

receive a charge imbalance parameter that sets a charge imbalance between the positive phase and the negative phase of the waveform; and transmit information to the implantable stimulator device, wherein the information is configured to program the implantable stimulator device to provide the waveform as charge imbalanced by the charge imbalance parameter to at least two of the electrodes.

2. The system of claim 1, wherein the plurality of parameters comprise at least one of: an amplitude of the waveform, a pulse width of the waveform, a pulse width of the positive phase or the negative phase of the waveform, or a frequency at which waveforms are provided at the at least two electrodes.

3. The system of claim 1, wherein the control circuitry is further configured to receive a selection of the at least two electrodes.

4. The system of claim 1, wherein in the waveform, a total anodic current sourced to at least one of the at least two electrodes equals a total cathodic current sunk to at least one of the at least two electrodes.

5. The system of claim 1, wherein the charge imbalance parameter comprises a difference between the positive phase and the negative phase of the waveform.

6. The system of claim 5, wherein the difference comprises a difference in amplitude, a difference in pulse width, or a difference in charge.

7. The system of claim 5, where the difference is expressed as a ratio, a percentage, or a differential.

8. The system of claim 1, wherein the control circuitry is further configured to use the plurality of parameters and the charge imbalance parameter to determine a DC current, DC voltage or DC current density to be formed between the at least two electrodes.

9. The system of claim 1, further comprising the implantable stimulator device.

10. The system of claim 9, wherein the implantable stimulator device comprises a fully-implantable stimulator device, and wherein the implantable stimulator device comprises a conductive case, wherein one of the at least two electrodes comprises the conductive case.

11. The system of claim 9, wherein the implantable stimulator device comprises at least one lead that comprises the plurality of electrodes.

12. The system of claim 9, wherein the implantable stimulator device further comprises decoupling capacitors in series with the at least two electrodes.

13. A method for programming an implantable stimulator device comprising a plurality of electrodes configured to contact a patient's tissue, the method comprising:

defining at an external device a waveform comprising a positive phase and a negative phase;

setting at the external device a charge imbalance parameter that sets a charge imbalance between the positive phase and the negative phase of the waveform; and transmitting information from the external device to the implantable stimulator device, wherein the information is configured to program the implantable stimulator device to provide the waveform as charge imbalanced by the charge imbalance parameter to at least two of the electrodes.

14. The method of claim 13, wherein the charge imbalance parameter comprises a difference between the positive phase and the negative phase of the waveform.

15. The method of claim 14, wherein the difference comprises a difference in amplitude, a difference in pulse width, or a difference in charge.

16. The method of claim 14, where the difference is expressed as a ratio, a percentage, or a differential.

17. The method of claim 13, further comprising determining in the external device a DC current, DC voltage or DC current density to be formed between the at least two electrodes.

18. The method of claim 13, wherein the implantable stimulator device comprises at least one lead that comprises the plurality of electrodes.

19. The method of claim 13, wherein the implantable stimulator device further comprises decoupling capacitors in series with the at least two electrodes.

20. A non-transitory computer readable media comprising instructions executable on an external device for programming an implantable stimulator device, wherein the implantable stimulator device comprises a plurality of electrodes configured to contact a patient's tissue, wherein the instructions when executed are configured to enable control circuitry in the external device to:

receive a plurality of parameters defining a waveform, wherein each waveform comprises a positive phase and a negative phase;

receive a charge imbalance parameter that sets a charge imbalance between the positive phase and the negative phase of at least one waveform in the sequence of waveforms;

transmit information from the external device to the implantable stimulator device, wherein the information is configured to program the implantable stimulator device to provide the waveform as charge imbalanced by the charge imbalance parameter to at least two of the electrodes.

* * * * *